(12) United States Patent
Martins Borges et al.

(10) Patent No.: US 10,913,757 B2
(45) Date of Patent: Feb. 9, 2021

(54) HYDROXYCINNAMIC DERIVATIVES, METHODS AND USES THEREOF

(71) Applicants: UNIVERSIDADE DO PORTO, Oporto (PT); CENTRO DE NEUROCIÊNCIAS E BIOLOGIA CELULAR, Coimbra (PT)

(72) Inventors: Maria Fernanda Martins Borges, Oporto (PT); Paulo Jorge Gouveia Simões Da Silva Oliveira, Cantanhede (PT); JoséCarlos Santos Teixeira, Oporto (PT); Fernando Cagide Fagin, Oporto (PT); Ester Sofia Teixeira Benfeito, Oporto (PT)

(73) Assignees: UNIVERSIDADE DO PORTO, Oporto (PT); CENTRO DE NEUROCIÊNCIAS E BIOLOGIA CELULAR, Coimbra (PT)

( * ) Notice: Subject to any disclaimer, the term of this patent is extended or adjusted under 35 U.S.C. 154(b) by 0 days.

(21) Appl. No.: 16/342,083

(22) PCT Filed: Oct. 16, 2017

(86) PCT No.: PCT/IB2017/056412
§ 371 (c)(1),
(2) Date: Apr. 15, 2019

(87) PCT Pub. No.: WO2018/069904
PCT Pub. Date: Apr. 19, 2018

(65) Prior Publication Data
US 2019/0248816 A1 Aug. 15, 2019

(30) Foreign Application Priority Data
Oct. 14, 2016 (PT) .................................. 109680

(51) Int. Cl.
| | | |
|---|---|---|
| *C07F 9/54* | (2006.01) | |
| *A61P 9/04* | (2006.01) | |
| *A61P 25/02* | (2006.01) | |
| *A61P 31/00* | (2006.01) | |
| *A61K 8/55* | (2006.01) | |
| *A61K 47/36* | (2006.01) | |
| *A61K 47/26* | (2006.01) | |
| *A61K 47/10* | (2017.01) | |
| *A61Q 19/08* | (2006.01) | |
| *A61K 47/02* | (2006.01) | |

(52) U.S. Cl.
CPC .............. *C07F 9/5442* (2013.01); *A61P 9/04* (2018.01); *A61P 25/02* (2018.01); *A61P 31/00* (2018.01); *C07F 9/5456* (2013.01); *A61K 8/55* (2013.01); *A61K 47/02* (2013.01); *A61K 47/10* (2013.01); *A61K 47/26* (2013.01); *A61K 47/36* (2013.01); *A61Q 19/08* (2013.01)

(58) Field of Classification Search
CPC .................................. C07F 9/54; C07F 9/5442
See application file for complete search history.

(56) References Cited

U.S. PATENT DOCUMENTS

2013/0272983 A1 10/2013 Okombi et al.

FOREIGN PATENT DOCUMENTS

IL 237549 A * 9/2016

OTHER PUBLICATIONS

Teixera Jose et al, "Rational discovery and development of a mitochondria-targeted antioxidant based on cinnamic acid scaffold.", CA, Chemical Abstracts Service, Columbus, Ohio, US, Database accession No. 2012:447889, XP002777032 [XD] 1-4,10,23-36,39-45 * abstract * [A] 19,20,22 [I] 5-9,11-18,21,37,38,46,47 , 2012.
Teixeira J; Soares P; Benfeito S; Gaspar A; Garrido J; Murphy MP et al., "Rational discovery and development of a mitochondria-targeted antioxidant based on cinnamic acid scaffold", Free Radical Research, (2012), vol. 46, No. 5, pp. 600-611.
Prasipan N et al, "N-1 and C-2 Substituted Tryptophans as Potential Inhibitors of Sickle Cell Hemoglobin Gelation", Journal of Heterocyclic Chemistry, Wiley-Blackwell Publishing, Inc, US, (Mar. 1, 1992), vol. 29, No. 2, doi:10.1002/JHET.5570290210, ISSN 0022-152X, pp. 335-341, XP000984090 [X] 1-4,7,9,11,12 * Scheme 2 * , 1992.
Brovarets, V. S. et al, "Synthesis of [1-(acylamino)ethenyl]triphenylphosphonium salts", CA, Chemical Abstracts Service, Columbus, Ohio, US, Database accession No. 1993:102080, URL: STN, XP002777033 [X] 1,4 * abstract * , 1993.
Benfeito S; Oliveira C; Soares P; Fernandes C; Silva T; Teixeira J et al., "Antioxidant therapy: still in search of the 'magic bullet", Mitochondrion, (2013), vol. 13, No. 5, pp. 427-435, XP028696391 [ID] 1-4,9-11,13,23-47 * abstract * [A] 5-8,12,14-22.
Melissa Millard et al, "A Selective Mitochondrial-Targeted Chlorambucil with Remarkable Cytotoxicity in Breast and Pancreatic Cancers", Journal of Medicinal Chemistry, (Nov. 27, 2013), vol. 56, No. 22, doi:10.1021/im4012438, ISSN 0022-2623, pp. 9170-9179, XP055438311 [I] 1-4,23-47 * Scheme 1* , 2013.
Murphy MP. Antioxidants as therapies: can we improve on nature? Free Radical Biology and Medicine 2014, 66: 20-23.
Benfeito S, Oliveira C, Soares P, Fernandes C, Silva T, Teixeira J, et al. Antioxidant therapy: still in search of the magic bullet'. Mitochondrion 2013, 13(5): 427-435.

(Continued)

*Primary Examiner* — Laura L Stockton
(74) *Attorney, Agent, or Firm* — Leason Ellis LLP

(57) ABSTRACT

The present disclosure relates to the design and development of new hydroxycinnamic derivatives that operate as mitochondriotropic antioxidants. Furthermore, this disclosure is also related to the methods and uses of the hydroxycinnamic derivatives, for example, in the field of human and animal diseases, for instance to treat mitochondrial dysfunction or mitochondrial deficiencies, and cosmetics, for instance to prevent or delay skin aging.

22 Claims, 12 Drawing Sheets

(56) References Cited

OTHER PUBLICATIONS

Wallace DC, Fan W, Procaccio V. Mitochondrial energetics and therapeutics. Annual review of pathology 2010, 5: 297-348.
Smith RA, Hartley RC, Cocheme HM, Murphy MP. Mitochondrial pharmacology. Trends in pharmacological sciences 2012, 33(6): 341-352.
Silva T, et al. Caffeic acid derivatives, analogs and applications: a patent review (2009-2013). Expert Opin Ther Pat. Nov. 2014;24(11):1257-70. doi: 10.1517/13543776.2014.959492. Epub Oct. 4, 2014.
Alam MA, et al. Hydroxycinnamic acid derivatives: a potential class of natural compounds for the management of lipid metabolism and obesity. Nutr Metab (Lond). Apr. 11, 2016;13:27. doi: 10.1186/s12986-016-0080-3. eCollection 2016. Retirado da net: https://www.ncbi.nlm.nih.gov/pmc/articles/PMC4827240/ (Mar. 22, 2017).
Anders MW. Exploiting endobiotic metabolic pathways to target xenobiotic antioxidants to mitochondria. Mitochondrion. Sep. 2013;13(5):454-63. doi: 10.1016/j.mito.2012.10.015. Epub Nov. 1, 2012.
Chen YS, et al. Biological and structural studies of phosphonium 'masked thiolate' compounds. Eur J Med Chem. Jan. 5, 2017;125:528-537. doi: 10.1016/j.ejmech.2016.08.025.

* cited by examiner

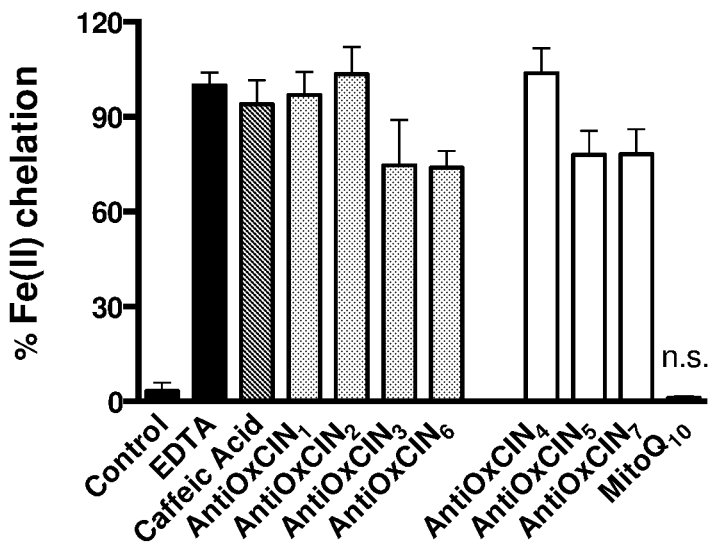
Fig. 2
Fig. 3A
Fig. 3B
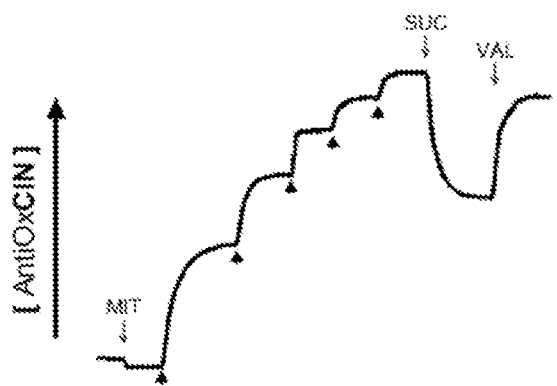
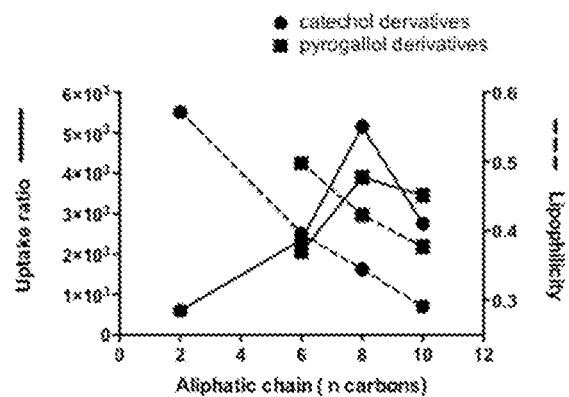
| Fig. 3C | [ Intramitochondrial ] (mM) | [ Extramitochondrial ] (µM) | Accumulation Ratio |
|---|---|---|---|
| AntiOxCIN$_1$ | 1.5 | 3.7 | 600 |
| AntiOxCIN$_2$ | 2.5 | 1.8 | 2500 |
| AntiOxCIN$_3$ | 5.7 | 1.2 | 5100 |
| AntiOxCIN$_6$ | 4.7 | 1.9 | 2700 |
| AntiOxCIN$_4$ | 2.0 | 2.4 | 2100 |
| AntiOxCIN$_5$ | 4.5 | 1.0 | 3900 |
| AntiOxCIN$_7$ | 5.0 | 1.4 | 3500 |

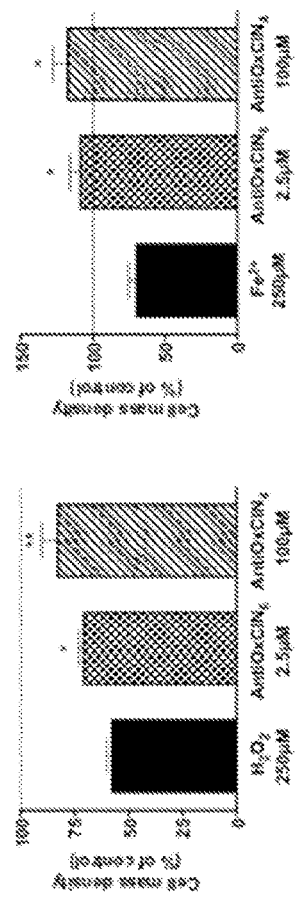
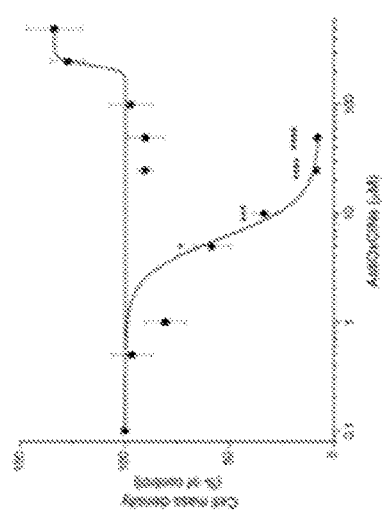
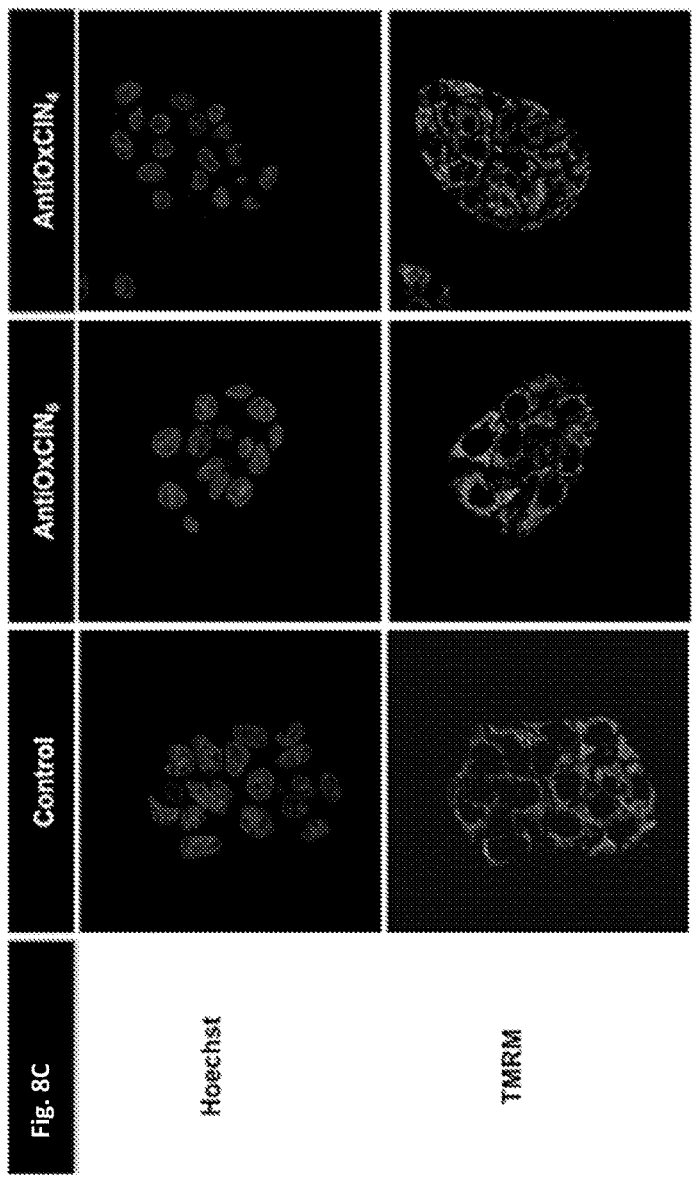

HYDROXYCINNAMIC DERIVATIVES, METHODS AND USES THEREOF

CROSS-REFERENCE TO RELATED PATENT APPLICATIONS

This is a U.S. National Phase Application under 35 U.S.C. § 371 of International Patent Application No. PCT/IB2017/056412, filed Oct. 16, 2017, and claims priority to Portuguese Patent Application No. 109680, filed Oct. 14, 2016. The International Application was published on Apr. 19, 2018, as International Publication No. WO/2018/069904 A1.

TECHNICAL FIELD

The present disclosure relates to the design and development of new hydroxycinnamic derivatives that operate as mitochondriotropic antioxidants. Furthermore, this disclosure is also related to the methods and uses of the hydroxycinnamic derivatives, for example, in the field of human and animal diseases, for instance to treat mitochondrial dysfunction or mitochondrial deficiencies, and cosmetics, for instance to prevent or delay skin aging.

BACKGROUND ART

Oxidative stress is a very complex process, which impacts biological systems in different aspects. Its impact on biological systems depends on the type of oxidant agent involved, on the site and intensity of its production, on the composition and activities of endogenous antioxidants, and on the activity of repair systems Oxidative stress can alter redox signalling in cells disrupting the normal homeostasis, which in some cases can lead to major cellular damage, thus being connected with a number of diseases, namely those associated with aging.[1,2]

In a pathological event, the pool of endogenous antioxidant defences may not be enough to deal with the increased oxidant production so it has been suggested that the administration of exogenous antioxidants can be beneficial to decrease cell injury, given that they not only compensate the insufficiency of endogenous defence systems but also improve the overall antioxidant response. Exogenous antioxidants may in theory block the complex networks of oxidative damage pathways at different levels, yielding an therapeutic effect. Consequently, antioxidants that are exogenously acquired from diet may have important functions in redox cell homeostasis and can be important for cellular function and disease prevention.

Antioxidants have been defined as any substance that when present at low concentrations, compared to those of an oxidizable substrate, significantly delays or prevents the oxidation of biomolecules. Antioxidants may exert their effects by different mechanisms, such neutralizing circulating reactive species (scavenging activity), sequestering transition metal ions (chelation activity) and inhibiting enzymes involved in the production of reactive species.[1,2] Moreover antioxidants may also increase the expression or activity of endogenous antioxidant systems.

The use of antioxidants, per se or in combination with other drugs, is considered to be beneficial for the prevention/minimization of deleterious events related with oxidative-stress, namely in associated diseases or processes[1].

Phenolic compounds are one of the most important classes of natural antioxidants present in the human diet. Epidemiological studies and associated meta-analyses suggested that the long-term consumption of diets rich in phenolic rich foods or beverages has a positive outcome in the incidence of oxidative-stress-related diseases[2].

Hydroxycinnamic acids (HCAs) are one of the major classes of phenolic compounds found in nature and in diet. Among HCAs, caffeic and coumaric acid are the most abundant in fruits accounting for between 75 and 100% of the total HCAs content. The dietary intake of HCAs has been estimated to be a total of 211 mg/day. In another study, and as an example, the intake of caffeic acid alone was reported to be 206 mg/day, being coffee, fruits and their juices the main dietary sources[2].

Hydroxycinnamic acids (HCAs) exhibit a wide range of biological activities. They are well-known by their antioxidant properties that are related with diverse action mechanisms, namely direct free radical scavenging activity and/or other indirect actions, including the chelation of pro-oxidant transition metals (namely copper and iron), modulation of gene expression (e.g. ARE/Nrf2 pathway) and inhibition of radical generating enzymatic systems[2].

Phenolic natural antioxidants, like hydroxycinnamic acids, have enjoyed general success in preclinical studies but still have little benefit in human intervention studies or clinical trials. In clinical trials over the past years no positive/relevant results were obtained so far. Most studies showed that some of them lacked any therapeutic advantage. In fact, a significant mismatch between the results obtained in pre-clinical studies and the outcome of clinical trials exists. This gap may be related not only with the protocol used in clinical trials but also by pharmacokinetics restrains of the antioxidants under evaluation assessment. Similarly to other natural or dietary antioxidants they have bioavailability drawbacks being unable to cross biological barriers and reach intracellular target sites[2]. On the other hand, some authors proposed that this type of natural antioxidants may alter the normal redox balance in particular cell compartments, which will make more harm than good. Another possibility is that some of the antioxidants do not reach the relevant places of free radical generation, namely mitochondria that are actually the primary source of reactive oxygen species (ROS) and oxidative damage[1,2].

Mitochondrial function, and specifically its impact in cellular redox/oxidative balance, is fundamental for controlling cellular life and death. Besides being the major source of chemical energy to the cell, mitochondria are involved in the production and detoxification of ROS, in the regulation of multiple signalling pathways related with cellular homeostasis, including cell survival, redox balance and cell death[3,4]. Although ROS production is tightly regulated by an endogenous antioxidant network, its disruption can lead to mitochondrial oxidative damage and dysfunction. Mitochondrial oxidative dysfunction impairs multiple metabolic and signalling pathways and can trigger cell death via apoptosis or necrosis.

Increasing evidence suggests that mitochondrial alterations resulting from augmented oxidative stress play a crucial role, for instance, in cancer, stroke, heart failure, obesity, neurodegenerative disorders and aging[3,4].

While the role of mitochondria in disease pathogenesis is rather consensual, targeting that organelle to prevent disruption is not always straightforward. Improvement of mitochondrial function through prevention/minimization of oxidative damage is an effective and promising therapeutic strategy. Since maintaining ROS/antioxidant ratio and redox maintenance is critical for cell signalling, targeting antioxidants to a dysfunctional mitochondria is of pharmacologic interest[3,4]

A number of mitochondria-targeted antioxidants are being developed, in particular those using triphenylphosphonium (TPP) as carrier. This type of lipophilic cation can cross the mitochondrial membrane and accumulate within the mitochondrial matrix taking advantage of the inner membrane electric potential gradient $(\Delta\Psi)^{2,4}$.

One of the most studied mitochondria-targeted antioxidants is Mitoquinone (MitoQ, $MitoQ_{10}$, [10-(4,5-dimethoxy-2-methyl-3,6-dioxo-1,4-cyclohexadien-1-yl)decyl] triphenylphosphonium methanesulfonate). MitoQ is constituted by an endogenous antioxidant moiety (coenzyme Q) covalently linked to a 10-carbon alkyl chain (dTPP) spacer and to a triphenylphosphonium (TPP) cation. MitoQ is under clinical trials for different pathologies, namely for hepatitis C. Yet, clinical trials using MitoQ as a therapeutic solution for neurodegenerative diseases have produced disappointing results.

Another relevant mitochondrial-targeted antioxidant is SKQ1 [10-(4,5-dimethyl-3,6-dioxocyclohexa-1,4-dien-1-yl) decyl)triphenylphosphonium bromide)], which is based on plastoquinone, a quinone involved in the electron transfer chain of chloroplasts. SkQ1 was shown to decrease oxidative stress inside mitochondria and significant protecting benefits for dry eye condition.

Nevertheless, there is still a need for effective and safe mitochondrial modulators to be used in therapy and in other applications such as cosmetic.

The use of TPP as carrier was also tracked as a strategy to target HCAs to mitochondria. In this context, a prototype of a mitochondrial-directed antioxidant based on caffeic acid was developed by our group[5]. The compound here named as $AntiOxCIN_1$, preserved the parent compound antioxidant activity while being more lipophilic. AntiOxCIN1 accumulated in mitochondria and protected mouse myoblast C2C12 cells against different oxidative stress stressors, namely $H_2O_2$ and linoleic acid-hydroperoxides However, AntiOxCIN1 efficacy as mitochondriotropic antioxidant was far from desired.

These facts are disclosed in order to illustrate the technical problem addressed by the present disclosure.

General Description

Mitochondria, and the control of the cellular reactive oxygen species (ROS) and redox balance, are an attractive target for drug discovery and development. Targeting mitochondria with modulator agents has proven to be an effective strategy. In this context, the rational design of potent and effective mitochondriotropic antioxidants (AntiOxCINs) based on hydroxycinnamic acids was performed.

The present disclosure, in a first aspect, is related to the development of new hydroxycinnamic derivatives that may be identified by the general formula

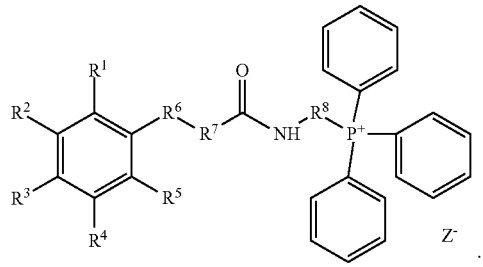

or a pharmaceutically acceptable salt, solvate, hydrate, tautomer, stereoisomer, wherein $R^1$, $R^2$, $R^3$, $R^4$, $R^5$, $R^6$, $R^7$ and $R^8$ are independently selected from each other;

$R^1$, $R^2$, $R^3$, $R^4$ and $R^5$ are selected from H, halogen, hydroxyl, methyl, methoxyl, amino, carboxylic acid, or nitro group;

$R^6$, $R^7$, $R^8$ are an alkyl chain, an alkenyl chain, an alkynyl chain, a substituted aryl or a cyclic ring;

a bond between $R^6$ and $R^7$ is a single bond, a double bond or a triple bond and with the proviso that wherein the bond between $R^6$ and $R^7$ is a double bond, $R^3$=$R^2$ are different from OH, and $R^1$=$R^4$ are different from H, and $R^6$=$R^7$ are different from methyl, and $Z^-$ is an anion.

Based on the International Union of Pure and Applied Chemistry (IUPAC) definitions, an alkyl group is defined as a univalent group derived from alkanes by removal of a hydrogen atom from any carbon atom —$C_nH_{2n+1}$. The groups derived by removal of a hydrogen atom from a terminal carbon atom of unbranched alkanes form a subclass of normal alkyl (n-alkyl) groups H $(CH_2)_n$. The groups $RCH_2$, $R_2CH$ (R≠H), and $R_3C$ (R≠H) are primary, secondary and tertiary alkyl groups, respectively. An aryl group is derived from arenes (monocyclic and polycyclic aromatic hydrocarbons) by removal of a hydrogen atom from a ring carbon atom.

"Alkyl" includes "lower alkyl" and extends to cover carbon fragments having up to 30 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

Halogen is an element selected from the list consisting of: F, Cl, Br, I, At.

In an embodiment, the bond between $R^6$ and re may be a single bond or a double bond, with the proviso that wherein the bond between $R^6$ and $R^7$ is a double bond, $R^3$=$R^2$ are different from OH, and $R^1$=$R^4$ are different from H, and $R^6$=$R^7$ are different from methyl.

In an embodiment, the alkyl chain, the alkenyl chain or the alkynyl chain may be a $C_1$-$C_{30}$ chain, preferably a $C_1$-$C_{18}$ chain, more preferably a $C_2$-$C_{14}$ chain, even more preferably a $C_3$-$C_{12}$ chain or a $C_6$-$C_{10}$ chain.

In an embodiment, the alkyl chain may be a $C_6$ alkyl chain, a $C_7$ alkyl chain, a $C_8$ alkyl chain, a $C_9$ alkyl chain, or a $C_{10}$ alkyl chain.

In an embodiment, the substituted aryl may be an alkane-aryl substituted, alkene-aryl substituted, or alkyne-aryl substituted preferably $C_6$-$C_{10}$-aryl, preferably phenyl; benzyl, phenethyl, phenpropyl, phenbutyl or phenhexyl, which is optionally substituted once or several times by:

a) $C_1$-$C_6$-alkyl, $C_3$-$C_8$-cycloalkyl, $C_6$-$C_{10}$-aryl, $C_6$-$C_{10}$-aryl-$C_1$-$C_8$-alkyl, $C_1$-$C_6$-alkoxy, $C_6$-$C_{10}$-aryloxy, $C_6$-$C_{10}$-aryl-$C_1$-$C_8$-alkoxy, hydroxyl, $CO_2H$, $C_1$-$C_6$-alkoxycarbonyl, $C_6$-$C_{10}$-aryloxycarbonyl, $C_6$-$C_{10}$-aryl-$C_1$-$C_8$-alkoxycarbonyl, $C_1$-$C_6$-alkylcarbonyl, $C_6$-$C_{10}$-arylcarbonyl, $C_6$-$C_{10}$-aryl-$C_1$-$C_8$-alkylcarbonyl, $C_1$-$C_6$-alkylcarboxy, $C_6$-$C_{10}$-arylcarboxy, $C_1$-$C_6$-alkylmercaptyl, $C_6$-$C_{10}$-arylmercaptyl, $C_1$-$C_6$-alkylmercaptocarbonyl, $C_3$-$C_8$-cycloalkylmercaptocarbonyl, $C_6$-$C_{10}$-arylmercaptocarbonyl, $C_1$-$C_6$-alkylmercaptocarboxy, $C_6$-$C_{10}$-arylmercaptocarboxy, $C_1$-$C_6$-alkylsulfonyl, $C_6$-$C_{10}$-arylsulfonyl, $C_1$-$C_6$-alkylsulfoxy, $C_6$-$C_{10}$-arylsulfoxy;

each of which is optionally substituted once or several times by $C_1$-$C_6$-alkyl, $C_1$-$C_6$-alkoxy, COOH; $CONH_2$, optionally substituted once or twice with $C_1$-$C_6$-alkyl; $SO_3H$, amino, thiol, hydroxyl, nitro, cyano, fluoro, chloro, bromo, iodo, $CF_3$ or $OCF_3$;

wherein several of these optional substituents may be combined to form anellated saturated, unsaturated or aromatic homo- or hetero-ring systems; or b) a saturated, unsaturated or aromatic heterocycle, optionally substituted once or several times by $C_1$-$C_6$-alkyl, $C_1$-$C_6$-alkoxy, COOH; $CONH_2$, optionally substituted once or twice.

In an embodiment, the cyclic ring may be a cyclopropane, cyclobutane, cyclopentane, or cyclohexane.

In an embodiment, the $Z^-$ anion is selected from the following list: alkyl sulfonate, aryl sulfonate, nitrate or a halogen, wherein said halogen may be F, Cl or Br; the alkyl sulfonate or aryl sulfonate may be selected from the following list: methanesulfonate, p-toluenesulfonate, ethanesulfonate, benzenesulfonate and 2-naphthalenesulfonate.

In an embodiment, $R^1$, $R^2$, $R^3$, $R^4$ and $R^5$ may comprise an halogen, wherein said halogen is F, Cl or Br.

In an embodiment, $R^1$ and $R^5$ may be H.

In an embodiment, $R^2$ and $R^3$ may be OH.

In an embodiment, $R^4$ may be H or OH.

In an embodiment, $R^6$ and $R^7$ may be a $C_1$ alkyl chain.

In an embodiment, $R^8$ may be a $C_2$ alkyl chain.

In an embodiment, the compound may be (E)-(6-(3-(3,4-dihydroxyphenyl)prop-2-enamido)hexyl)triphenylphosphonium methanesulfonate.

In an embodiment, the compound may be (E)-(8-(3-(3,4-dihydroxyphenyl)acrylamido)octyl)triphenylphosphonium-methanesulfonate.

In an embodiment, the compound may be (E)-(6-(3-(3,4,5-trihydroxyphenyl)prop-2-enamido)hexyl)triphenylphosphonium methanesulfonate.

In an embodiment, the compound may be (E)-(8-(3-(3,4,5-trihydroxyphenyl)acrylamido)octyl)triphenylphosphonium methanesulfonate.

In an embodiment, the compound may be (E)-(10-(3-(3,4-dihydroxyphenyl)acrylamido)decyl)triphenylphosphonium methanesulfonate.

In an embodiment, the compound may be (E)-(10-(3-(3,4,5-trihydroxyphenyl)acrylamido)decyl)triphenylphosphonium methanesulfonate.

The present disclosure also relates to any compound, or related ones, now disclosed for use in medicine or veterinary.

In an embodiment, the disclosed compounds, or related ones, may be used for modulating at least one aspect of mitochondrial morphology and/or expression of OXPHOS enzymes.

In an embodiment, the disclosed compounds, or related ones, may be used for the treatment or prevention or suppression of symptoms associated with a mitochondrial disorder or with a condition associated with mitochondrial dysfunction in general, including diseases originated from mitochondrial respiratory chain defects.

In an embodiment, the mitochondrial disorder is a disorder selected from the group consisting of: Myoclonic epilepsy; Myoclonic Epilepsy with Ragged Red Fibers (MERRF); Leber's Hereditary Optic Neuropathy (LHON); neuropathy ataxia and retinitis pigmentosa (NARP); Mitochondrial Myopathy, Encephalopathy, Lactacidosis, Stroke (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); myopathy; mitochondrial myopathy; cardiomyopathy; and encephalomyopathy, SURF1 (COX deficient Leigh syndrome due to complex IV surfeit protein deficiency) and isolated or combined OXPHOS deficiencies with so far unsolved genetic defect including disturbed pyruvate oxidation and ATP plus PCr production rates.

In an embodiment, the condition associated with mitochondrial dysfunction may be a disorder selected from the group consisting of: Friedreich's Ataxia (FRDA); renal tubular acidosis; Parkinson's disease; Alzheimer's disease; amyotrophic lateral sclerosis (ALS); Huntington's disease; developmental pervasive disorders; hearing loss; deafness; diabetes; ageing; and adverse drug effects hampering mitochondrial function.

In an embodiment, the compounds now disclosed, or related ones, may be for use in the treatment or prevention of a neurodegenerative disease, neoplasia, kidney disease, scleroderma, hepatic iron overload disease, hepatic copper overload disease, alopecia, human infertility, acute pancreatitis, fibromyalgia, or other disease related with the involvement of mitochondrial oxidative disease.

In an embodiment, the compounds now disclosed, or related ones, may be for use in the treatment of non-alcoholic fatty liver diseases, namely non-alcoholic fatty liver disease (NAFLD), non-alcoholic steatohepatitis (NASH), or hepatic cirrhosis, among others.

In an embodiment, the compounds now disclosed, or related ones, may be for use in neoplasias, namely wherein the neoplasia disease is a cancer, in particular basal cell carcinoma, bone cancer, bowel cancer, brain cancer, breast cancer, cervical cancer, leukemia, liver cancer, lung cancer, lymphoma, melanoma, ovarian cancer, pancreatic cancer, prostate cancer, thyroid cancer or biliary cancer, among others.

In an embodiment, the compounds now disclosed, or related ones, may be for use in kidney related diseases namely, kidney failure, among others.

In an embodiment, the compounds now disclosed, or related ones, may be for use in amyotrophic lateral sclerosis.

In an embodiment, the compounds now disclosed, or related ones, may be for use as antimicrobial agent, in particular as a disinfectant.

In an embodiment, the compounds now disclosed, or related ones, may be for use in the maintenance of a pluripotent cell culture, as a supplement for cell culture in particular as growth medium component.

In an embodiment, the compounds now disclosed, or related ones, may be for use for accelerating muscle recovery after physical exercise.

In an embodiment, the compounds now disclosed, or related ones, may be used as active ingredients on cosmetic, supplement or nutraceutical products, namely as an anti-aging or anti-wrinkle skin care ingredient or product.

In an embodiment, the compounds now disclosed, or related ones, may be for use as a probe in imaging studies, in particular to monitor mitochondrial imaging studies.

This disclosure also relates to a cell culture medium for maintaining pluripotent stem cells in an undifferentiated state comprising any of the compounds, or related ones, now disclosed.

This disclosure also relates to a pharmaceutical composition comprising any of the compounds, or related ones, now disclosed and one or more pharmaceutically acceptable carrier, adjuvant, excipient, diluent or mixtures thereof, among others.

In an embodiment, the pharmaceutically acceptable carrier may be selected from the following list: saline, gum acacia, gelatin, starch paste, talc, keratin, colloidal silica, urea or mixtures thereof, among others.

In an embodiment, the adjuvant may be selected from the following list: oil-in-water emulsion adjuvant, aluminium adjuvant, a TLR-4 ligand, a saponin, and mixtures thereof, among others.

In an embodiment, the excipient may be selected from the following list: glucose, lactose, sucrose, glycerol monostearate, sodium chloride, glycerol, propylene, glycol, water, ethanol or mixtures thereof, among others.

In an embodiment, the pharmaceutical composition may be topically, orally, parenterally or injectable administrated.

In an embodiment, the pharmaceutical composition may be for use, for example, in a method for the treatment or prevention of a neurodegenerative disease, non-alcoholic fatty liver disease, neoplasia, kidney disease, scleroderma, hepatic iron overload disease, hepatic copper overload disease, alopecia, human infertility, acute pancreatitis or fibromyalgia, wherein the pharmaceutical composition is administered in a daily dose.

In an embodiment, the daily dose of said pharmaceutical composition may be 20 mg/day or 10 mg/day, among others.

This disclosure also provides a nanocarrier, for instance a liposome, wherein said nanocarrier or said a liposome comprise the compounds, or related ones, or the pharmaceutical composition, now disclosed.

In some embodiments, the composition may comprise the compounds disclosed, or related ones, in the present subject-matter, in an amount effective to improve the efficacy of other therapies, including immunotherapy or any pharmacological approach, by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the composition comprises a dose of 0.1-1000 mg. For example, in some embodiments, the preparation comprises a dose of 0.1 mg/kg, 0.2 mg/kg, 0.3 mg/kg, 0.4 mg/kg, 0.5 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, or 1000 mg/kg. In some embodiments, the composition comprises a dose of 0.1-10 mg/kg, 0.1-100 mg/kg, 1-10 mg/kg, 1-100 mg/kg, 1-1000 mg/kg, 10-100 mg/kg, 10-1000 mg/kg, 100-1000 mg/kg, 10-50 mg/kg, 10-25 mg/kg, 10-20 mg/kg, 50-100 mg/kg, or 100-250 mg/kg.

Preferred routes of administration include but are not limited to oral, parenteral, intramuscular, intravenous, in situ injection, intranasal, sublingual, intratracheal, inhalation or topical.

In some embodiments, the dose or dosage form may be administered to the subject, for example, once a day, twice a day, or three times a day. In other embodiments, the dose is administered to the subject once a week, once a month, once every two months, four times a year, three times a year, twice a year, or once a year.

Throughout the description and claims the word "comprise" and variations of the word, are not intended to exclude other technical features, additives, components, or steps. Additional objectives, advantages and features of the solution now disclosed will become apparent to those skilled in the art upon examination of the description or may be learned by practice of the solution.

BRIEF DESCRIPTION OF THE DRAWINGS

The following figures provide preferred embodiments for illustrating the description and should not be seen as limiting the scope of disclosure.

FIG. 2: Evaluation of iron chelating properties of caffeic acid, AntiOxCINs and MitoQ. EDTA (chelating agent) was used as reference. Statistically significant compared with control group using one-way ANOVA ($P<0.0001$, n.s., not significant).

FIG. 3: (A) AntiOxCINs uptake by energised rat liver mitochondria measured using a TPP-selective electrode. (B) AntiOxCINs aromatic ring pattern substitution and alkyl carbon side chain effects on lipophilicity (---) and mitochondrial accumulation ratio (—). (C) AntiOxCINs accumulation ratio by rat liver mitochondria. MIT, mitochondria; SUC, succinate; VAL, valinomicin.

FIG. 8: (A) Cytotoxicity profile of $AntiOxCIN_4$ (■) and $AntiOxCIN_6$ (•) on hepatocellular carcinoma cells (HepG2). Statistically significant compared with control group using one-way ANOVA (B) Effect of $AntiOxCIN_4$ and AntiOx- $CIN_6$ on iron- and hydrogen peroxide-induced damage of HepG2 cells. The comparisons were performed by using one-way ANOVA between the control ($FeSO_4$ or $H_2O_2$) vs. preparation where AntiOxCINs were pre-incubated (C) $AntiOxCIN_4$ and $AntiOxCIN_6$ (100 μM and 2.5 μM, respectively) did not disturb the normal nuclear morphology and mitochondrial polarization.

DETAILED DESCRIPTION

Figure 1:
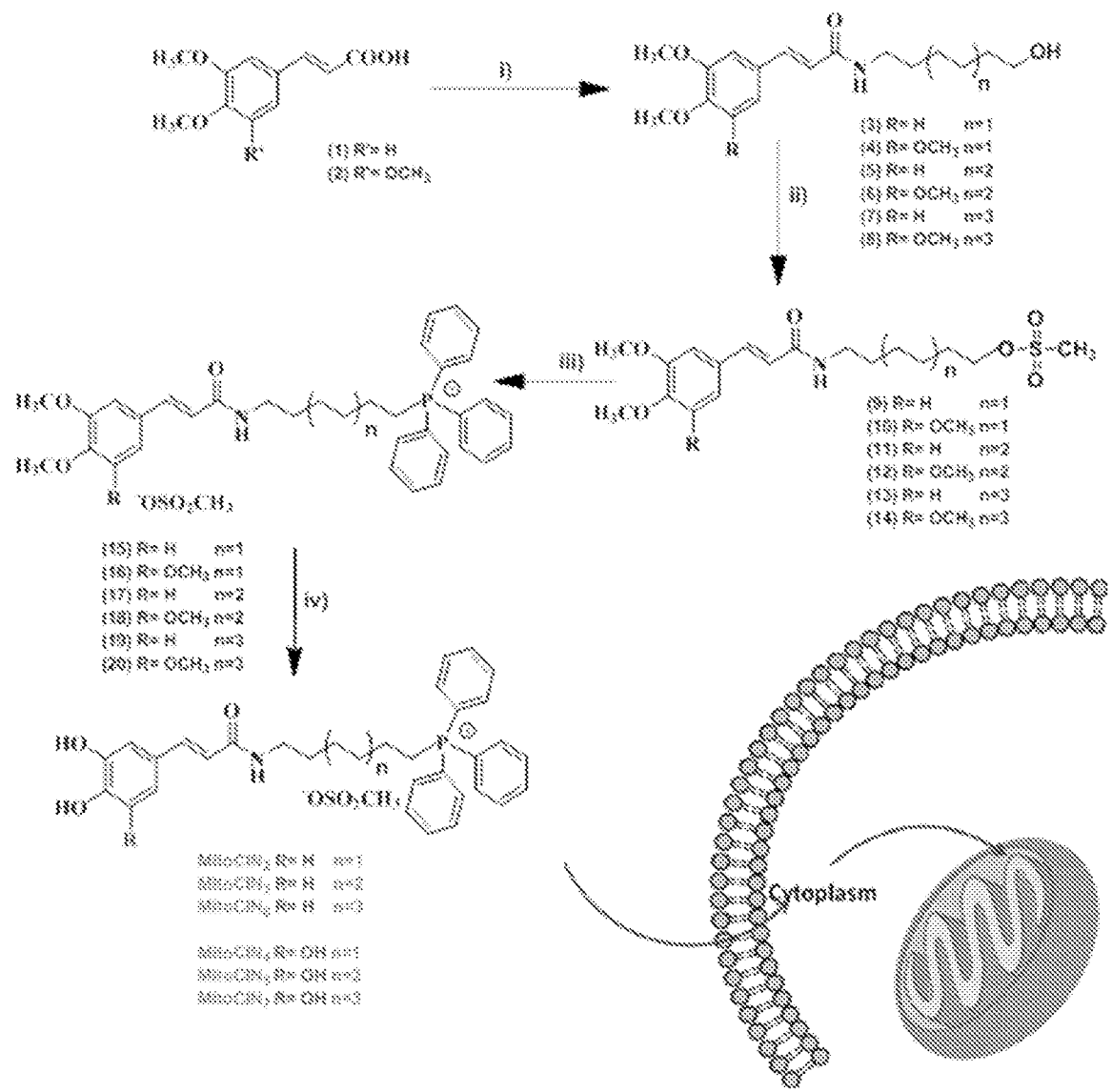
FIG. 1: Synthetic strategy pursued to obtain a number of AntiOxCINs. Reagents and conditions: i) Ethyl chloroformate, aminoalcohol, r.t.; ii) Methanesulfonyl chloride, r.t.; iii) Triphenylphosphine, 150° C. (microwave, 1 h 30 min) or 130° C. (18 h); or iv) BBr3, from −70° C. (10 min) to r.t. (12 h).

In an embodiment, and as an example the synthetic strategy pursued for the development of a number of cinnamic lipophilic cationic antioxidants (AntiOxCINs) is depicted in FIG. 1. In this example the di (1) or trimethoxy-cinnamic (2) acids used as starting materials were linked by an amidation reaction to suitable bifunctionalized alkyl spacers with a variable length (cinnamic derivatives 3-8). Then, the alcohol functions of the derivatives were activated with a leaving group (—$OSO_2CH_3$) to obtain the cinnamic derivatives 9-14. Afterward the terminal group was displaced via a nucleophilic substitution reaction with triphenylphosphine ($PPh_3$) to attain the triphenylphonium cations 15-20 throughout classic or microwave-assisted reactions. The use of microwave radiation allows obtaining AntiOxCINs precursors in an accelerated environmentally friendly process. The reaction time was of 1 hour and 30 minutes, in contrast with 18 h needed in the classic reaction. Finally, AntiOxCINs ($AntiOxCIN_2$ to $AntiOxCIN_2$) were obtained by a demethylation reaction using tribromide ($BBr_3$) solution.

In an embodiment, and as an example, the AntiOxCINs antioxidant, redox and lipophilic properties were reported. Caffeic acid and $AntiOxCIN_1$ were also included in the study. The results were depicted in Table 1.

TABLE 1

Antioxidant, redox and lipophilic properties of AntiOxClNs.

| Compound | MW (gmol$^{-1}$) | IC$_{50}$ (μM) | | | $E_p$ (V) | $E_{tr}$/V |
| | | DPPH· | ABTS·+ | GO· | | |
| --- | --- | --- | --- | --- | --- | --- |
| Caffeic acid | 180.16 | 18.1 | 17.9 | 3.4 | 0.168 | — |
| AntiOxCIN$_1$ | 563.60 | 35.4 | 33.3 | 4.5 | 0.166$^{a)}$ | 0.572 |
| AntiOxCIN$_2$ | 619.71 | 29.5 | 30.5 | 4.1 | 0.164 | 0.396 |
| AntiOxCIN$_3$ | 632.52 | 28.0 | 27.9 | 2.8 | 0.170 | 0.345 |
| AntiOxCIN$_6$ | 675.81 | 25.9 | 23.5 | 2.7 | 0.174 | 0.291 |
| AntiOxCIN$_4$ | 635.71 | 19.0 | 12.2 | 3.1 | 0.034 | 0.498 |
| AntiOxCIN$_5$ | 663.76 | 14.7 | 8.7 | 2.3 | 0.046 | 0.423 |
| AntiOxCIN$_7$ | 691.82 | 13.7 | 7.5 | 2.5 | 0.057 | 0.377 |

In an embodiment, the AntiOxCINs antioxidant ranking activity hierarchy was established by in vitro non-cell methods. The selected total antioxidant capacity (TAC) assays (DPPH, ABTS and GO) involved the spectrophotometric measurement of the radical absorbance decrease as a result of an in situ radical deactivation by an antioxidant. Compounds with higher antioxidant activity display lower $IC_{50}$ values. The antioxidant data (Table 1) allow concluding that AntiOxCINs are effective antioxidants, when compared with caffeic acid and $AntiOxCIN_1$, and that the attained $IC_{50}$ values followed the same trend in the three different assays. The data clearly indicated that the series comprising a pyrogallol system ($AntiOxCIN_4$, AntiOxCINs and $AntiOxCIN_7$) display a higher antioxidant activity than their catechol ($AntiOxCIN_2$, $AntiOxCIN_3$ and $AntiOxCIN_6$) counterparts In general, the introduction of the triphenylphosphonium (TPP) aliphatic side chain led to a slight decrease in the antioxidant activity, when compared to caffeic acid. This decrease was attenuated/ameliorated by the increment of the spacer length and/or the introduction of additional hydroxyl group in the aromatic ring.

In an embodiment, $AntiOxCIN_4$, $AntiOxCIN_5$ and $AntiOxCIN_7$ have a similar, or superior, antioxidant activity than caffeic acid and $AntiOxCIN_1$. The chemical changes performed in the spacer length do not have a negative influence in the radical-scavenging ability. On contrary a higher antioxidant capacity was observed for compounds that have a lengthy alkyl spacer.

In an embodiment, and as an example, AntiOxCINs redox properties were evaluated (Table 1). Redox potentials are correlated with the ability of an antioxidant to donate a hydrogen atom and/or an electron to a free radical. Generally, low oxidation potentials (Ep) are associated with a superior antioxidant performance.

In an embodiment, the redox data, attained at physiological pH (7.4) by differential pulse and cyclic voltammetry, allow concluding that caffeic acid and its catechol analogues ($AntiOxCIN_1$, $AntiOxCIN_2$, $AntiOxCIN_3$ and $AntiOxCIN_6$) showed redox potentials ($E_p$) characteristic of the presence of a catechol group ($E_p$=0.164-0.174 V) (Table 1). However, for pyrogallol derivatives ($AntiOxCIN_4$, $AntiOxCIN_5$ and $AntiOxCIN_7$), a significant decrease in redox potentials was observed ($E_p$=0.034-0.057 V) (Table 1).

In an embodiment, cyclic voltammetry data allowed concluding that caffeic acid and its catechol analogues ($AntiOxCIN_1$, $AntiOxCIN_2$, $AntiOxCIN_3$ and $AntiOxCIN_6$) suffer a reversible reaction, as a single anodic peak and one cathodic peak in the reverse scan was observed. In all systems the oxidation mechanism was comparable to that proposed for caffeic acid as it involved two electrons per molecule, which likely corresponded to the formation of a semiquinone radical and its subsequent oxidation to ortho-quinone.

In an embodiment, pyrogallol systems ($AntiOxCIN_4$, $AntiOxCIN_5$ and $AntiOxCIN_7$) appear to suffer an irreversible oxidation reaction as any reduction wave was seen on the cathodic sweep. For this type of systems, only one anodic peak was observed at physiological pH using differential pulse voltammetry. The voltammograms presented a diffusion peak and an adsorption post-peak at a more anodic potential correspondent to the oxidation of dissolved and adsorbed forms of the compounds, respectively. The oxidation waves can be related to the oxidation process of the pyrogallol moiety. The cyclic voltammograms also show the presence of two overlapped anodic peaks. The anodic peaks appeared to correspond to irreversible processes as any distinct reduction wave was not seen on the cathodic sweep. The existence of the additional phenolic group in the pyrogallol systems, when compared with the catechol ones, seems to influence the stabilization of the semiquinone intermediate and in turn the oxidative mechanism.

In an embodiment, the data attained with TAC assays is consistent with AntiOxCINs redox outline. Overall the results reinforce the assumption that the number of hydroxyl substituents present on the cinnamic aromatic ring is directly related with the antioxidant and electrochemical properties.

In an embodiment, AntiOxCINs lipophilic properties were evaluated at physiological pH by electrochemistry. The used technique is often used to mimic the transfer of ionic drugs through biological membranes as the process occurs at the interface between two immiscible electrolyte solutions (ITIES). The transfer potential ($E_{tr}$) at which the ionic drug, initially present in the aqueous phase (C=0.32 mM), is transferred to the 1,6-dichlorohexane (DCH) phase is measured by differential pulse voltammetry (DPV). In the ITIES model, the transfer potential ($E_{tr}$) becomes less positive with the increasing of the drug lipophilic character.

In an embodiment, and as an example, the AntiOxCINs transfer potentials ($E_{tr}$) obtained are shown in Table 1. In general, an increment of AntiOxCINs lipophilicity was observed as function of the length of the alkyl spacer. This behaviour was observed in both AntiOxCINs series, being AntiOxCIN$_1$ the less lipophilic compound. As expected, caffeic acid does not permeate. For catechol based series, the relative lipophilicity increased in the following order: AntiOxCIN$_1$<AntiOxCIN$_2$<AntiOxCIN$_3$<AntiOxCIN$_6$ and for pyrogallol based series: AntiOxCIN$_4$<AntiOxCIN$_5$<AntiOxCIN$_7$. For the same increment of spacer length (e.g. AntiOxCIN$_6$ vs AntiOxCIN$_2$) the introduction of an additional OH function increased AntiOxCINs hydrophilicity.

In an embodiment, and as an example, AntiOxCINs chelating properties, namely their ability to chelate iron, were determined. Iron is a redox active metal that can catalyse Fenton and Haber-Weiss reactions generating hydroxyl radicals (*OH), which is a strong oxidant species that is linked with oxidative damage events with severe implications for human health and disease. To note that loss of mitochondrial iron homeostasis and consequent iron overload can contribute to mitochondrial dysfunction and in turn to different pathologies. So, the use of metal chelating agents, or antioxidants that operate by this or more than one mechanism can function as a therapeutic approach to prevent metal-induced toxicity.

In an embodiment, AntiOxCINs iron (II) chelating properties were evaluated by the ferrozine assay using ethylenediaminetetracetic acid (EDTA) as reference. The iron chelating properties of caffeic acid and MitoQ were also evaluated. EDTA was found to be able to chelate all the iron in solution as it can inhibit completely the formation of the colored ferrozine-fe(II) complex.

In an embodiment, AntiOxCINs (catechol or pyrogallol series) and caffeic acid, in opposition to MitoQ, were able to chelate ferrous iron alike EDTA (FIG. 2). Despite the chemical modifications performed on AntiOxCINs, the new derivatives still present a noteworthy capacity to chelate iron, similarly to the chelating agent EDTA and to caffeic acid (FIG. 2). AntiOxCIN$_2$ and AntiOxCIN$_4$ displayed a higher iron chelation activity than caffeic acid itself.

In an embodiment, it is highlighted that AntiOxCINs chelating properties were not shared by MitoQ. This particular AntiOxCINs property may constitute per si an important feature for the treatment of mitochondrial and metabolic disorders involving iron overload.

In an embodiment, and as an example, mitochondrial AntiOxCINs uptake was assessed in isolated rat liver mitochondria (RLM) in response to the membrane potential. AntiOxCINs can accumulate inside mitochondria driven by the $\Delta\Psi$ (FIG. 3A). Different AntiOxCINs accumulation outlines within the mitochondrial matrix have been noticed. The process was found to be related with the increment of the spacer length and aromatic substitution pattern, and directly related with AntiOxCINs lipophilicity (FIGS. 3B and 3C, Table 1). However, the linear increase of AntiOxCINs lipophilicity was not directly translated into an increase in the ratio of mitochondrial matrix accumulation (FIG. 3B). The following ranking order was attained: AntiOxCIN$_1$<AntiOxCIN$_2$<AntiOxCIN$_6$<AntiOxCIN$_3$ (catechol series); AntiOxCIN$_4$<AntiOxCIN$_7$<AntiOxCIN$_6$ (pyrogallol series) (FIG. 3C). Although AntiOxCIN$_6$ and AntiOxCIN$_7$ were the most lipophilic compounds, they exhibit a lower accumulation ratio probably due to the cut-off membrane effect. Despite the chemical structural differences AntiOxCIN$_2$, AntiOxCIN$_6$ and AntiOxCIN$_4$ displayed approximately the same accumulation ratio. All AntiOxCINs present an accumulation ratio comparable to that of MitoQ and higher than AntiOxCIN$_1$ (FIG. 3C).

Mitochondrial membranes possess a high concentration of polyunsaturated fatty acids that are particularly prone to oxidation as they are located near to ROS producing sites.

In an embodiment, and as an example, AntiOxCINs antioxidant performance, on the protection of lipid peroxidation of RLM membranes was determined. Two different oxidative stressor agents, FeSO$_4$/H$_2$O$_2$/ascorbate and ADP/FeSO$_4$, and two end-points, TBARS production and oxygen-consumption, respectively, have been used. MitoQ was used as reference (FIGS. 4 and 5).

Figure 4A:
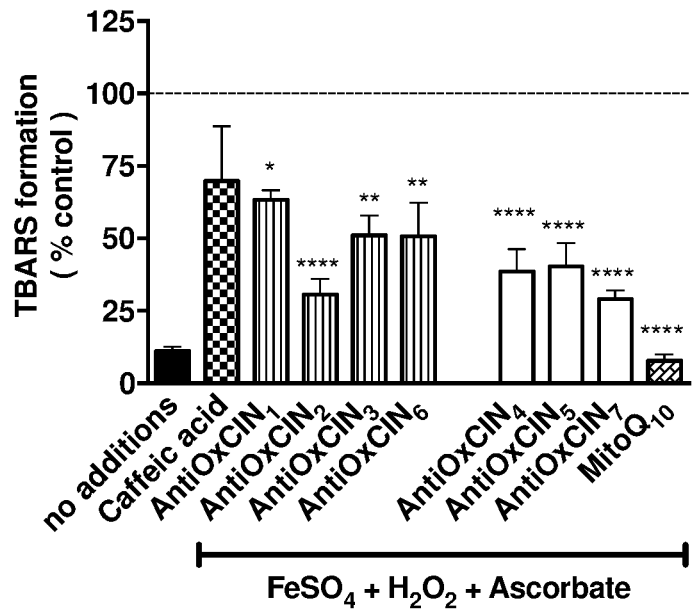
FIG. 4: Effect of caffeic acid, AntiOxCINs and MitoQ on mitochondrial lipid peroxidation under different oxidative conditions: (A) TBARS levels and (B) changes on oxygen consumption. The comparisons between control vs. AntiOxCINs (5 µM) pre-incubations were performed by using one-way ANOVA.
Figure 4B:
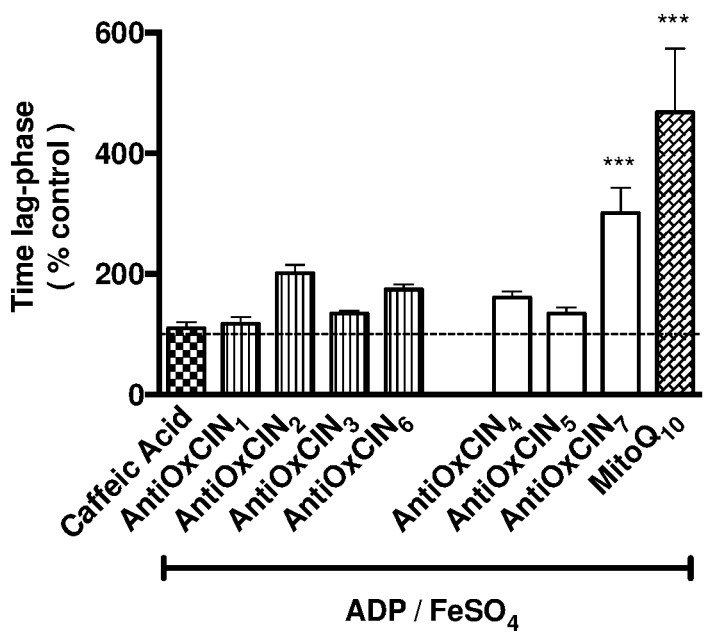
Figure 5A:
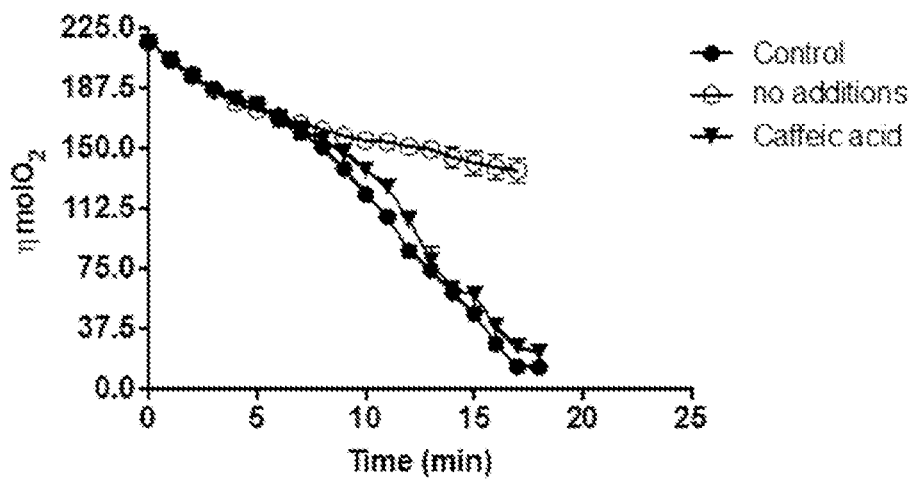
FIG. 5: Effect of (A) caffeic acid, (B) dTPP and MitoQ, and AntiOxCINs containing a (C) catechol or (D) pyrogallol core on lipid peroxidation of RLM membranes induced by ADP and $Fe^{2+}$ followed by oxygen consumption.
Figure 5B:
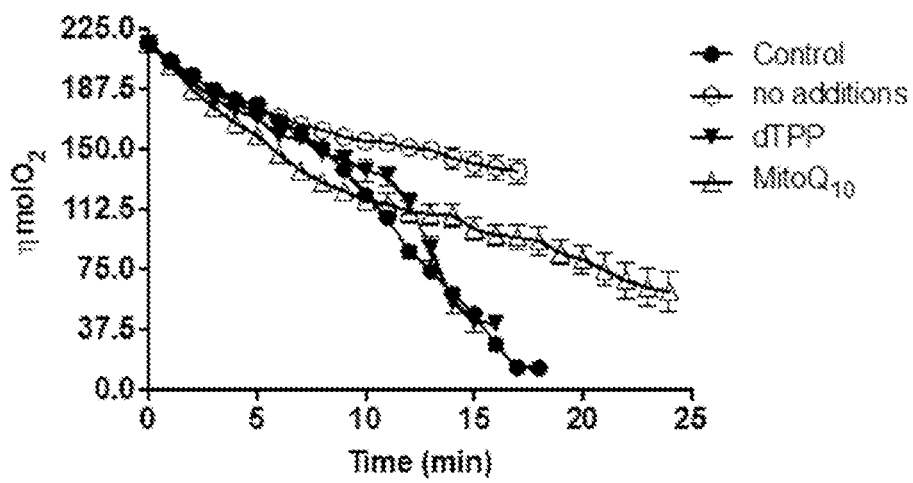
Figure 5C:
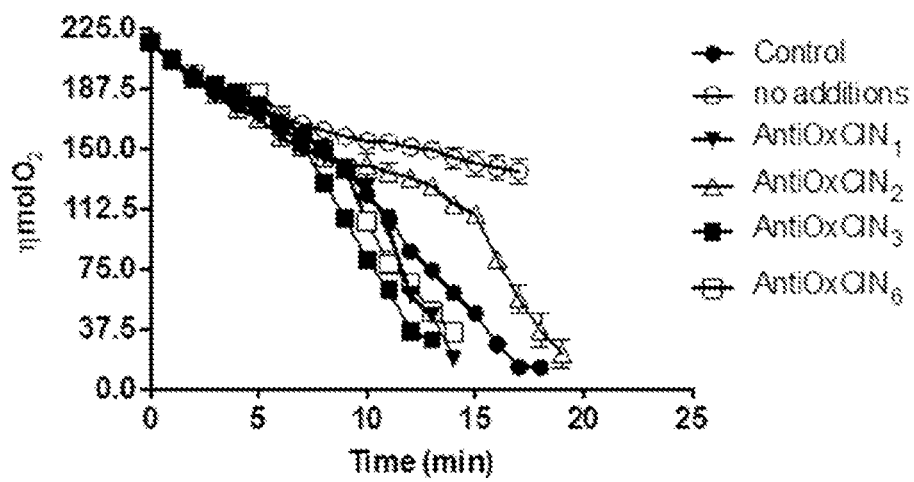
Figure 5D:
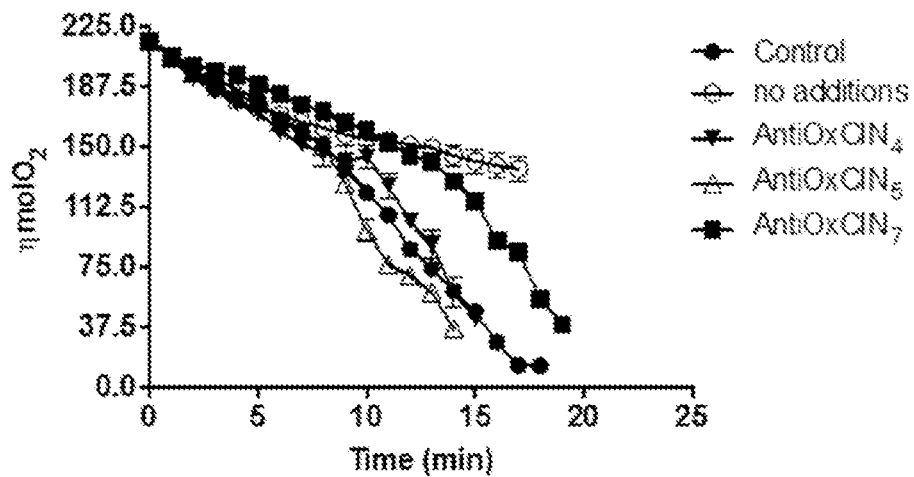

In an embodiment, AntiOxCIN$_2$ (catechol series) and AntiOxCIN$_2$ (pyrogallol series), in FeSO$_4$/H$_2$O$_2$/ascorbate assay, were found to be the most effective mitochondriotropic cinnamic derivatives in preventing mitochondria lipid peroxidation (FIG. 4A). In ADP/FeSO$_4$ assay AntiOxCINs efficiency to prevent lipid peroxidation followed the same tendency (FIGS. 4B and 5A-D). The ability of AntiOxCINs vs MitoQ to inhibit lipid peroxidation in RLM decreased in the order MitoQ>AntiOxCIN$_2$>AntiOxCIN$_2$>> AntiOxCIN$_4$≈AntiOxCIN$_5$>AntiOxCIN$_6$ z AntiOxCIN$_3$>AntiOxCIN$_1$>caffeic acid. Except for AntiOxCIN$_2$, pyrogallol based AntiOxCINs (FIGS. 4 and 5D) were more effective in delaying lipid peroxidation membrane process having a higher performance than caffeic acid.

As cellular metabolism depends on mitochondrial proper function the compounds' effects on mitochondria functional parameters can give information about their toxicity profile. So, their capacity to induce mitochondrial dysfunction by damaging the inner mitochondrial membrane or by inhibiting the respiratory chain, ATP synthesis, mitochondrial permeability transition pore (mPTP) process or export machinery was evaluated.

In an embodiment, and as an example, AntiOxCINs and MitoQ toxicity effects on the mitochondrial bioenergetics, namely on RLM $\Delta\Psi$ and mitochondrial respiration parameters, were measured. The ALP represents the main component of the electrochemical gradient generated by mitochondrial respiration and accounts for more than 90% of the total available energy. For mitochondrial respiration assays, glutamate/malate (for complex I) and succinate (for complex II) were used as substrates. In addition, the mitochondrial oxidative phosphorylation coupling index, known as respiratory control ratio (RCR, state 3/state 4 respiration) and ADP/O index (the coupling between ATP synthesis and oxygen consumption) were also calculated. AntiOxCINs and MitoQ were tested at antioxidant-relevant concentrations, with 10 μM being the highest concentration.

In an embodiment, the mitochondrial bioenergetics data obtained for MitoQ was shown in (Table 2). The results obtained have been used for comparative analysis.

TABLE 2

Effect of MitoQ on mitochondrial bioenergetics: mitochondrial respiratory control ratio (RCR), efficiency of the phosphorylative system (ADP/O), and mitochondrial transmembrane potential ($\Delta\Psi$).

| | Mitochondrial Bioenergetics | Control | MitoQ 2.5 µM | MitoQ 5 µM | MitoQ 10 µM |
|---|---|---|---|---|---|
| Glutamate/Malate | Maximum potential ($\Delta\Psi$ in - mV) | 225.8 ± 9.8 | 195.7 ± 10.8 | 188.3 ± 10.6 * | 113.9 ± 10.2 **** |
| | ADP-induced depolarization ($\Delta\Psi$ in - mV) | 194.2 ± 7.9 | 173.0 ± 9.3 | 173.5 ± 8.9 | |
| | Repolarization Potential ($\Delta\Psi$ in - mV) | 223.0 ± 9.7 | 191.1 ± 11.7 | 185.0 ± 9.4 * | |
| | Lag Phase (s) | 70.7 ± 6.0 | 86.5 ± 5.6 | 84.5 ± 7.1 | |
| | RCR | 6.4 ± 0.6 | 4.2 ± 0.6 * | 2.7 ± 0.3 *** | 1.3 ± 0.1 **** |
| | ADP/O | 2.6 ± 0.1 | 2.2 ± 0.1 * | 1.9 ± 0.1 *** | 2.0 ± 0.2 ** |
| Succinate | Maximum potential ($\Delta\Psi$ in - mV) | 202.1 ± 6.7 | 181.6 ± 8.3 | 170.2 ± 8.1 * | 108.9 ± 3.8 **** |
| | ADP-induced depolarization ($\Delta\Psi$ in - mV) | 173.9 ± 5.3 | 162.1 ± 6.0 | 157.0 ± 6.4 | |
| | Repolarization Potential ($\Delta\Psi$ in - mV) | 195.9 ± 5.5 | 182.7 ± 9.1 | 170.8 ± 8.7 * | |
| | Lag Phase (s) | 106.0 ± 12.4 | 104.8 ± 9.9 | 92.6 ± 19.4 | |
| | RCR | 4.9 ± 0.7 | 2.6 ± 0.2 ** | 2.4 ± 0.2 ** | |
| | ADP/O | 1.6 ± 0.1 | 1.3 ± 0.1 * | 1.3 ± 0.1* | |

*, , *, **** Statistically significant compared with control using Student's two tailed t-test.

Figure 6A:
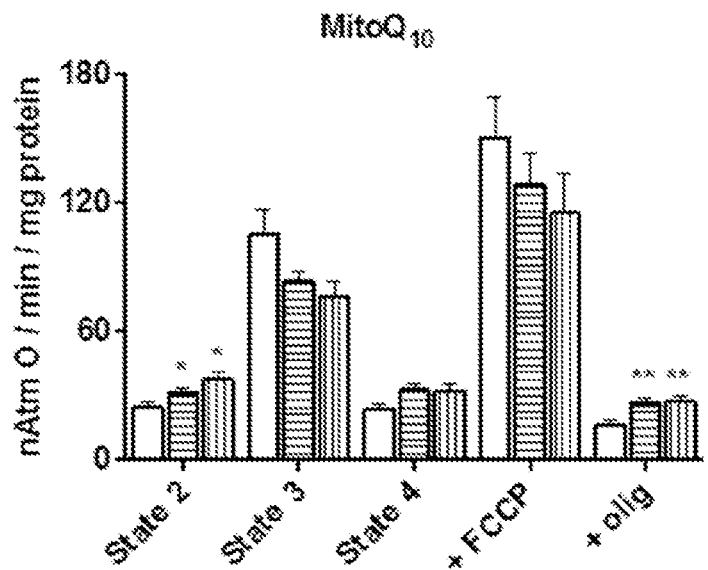
FIG. 6: Effect of MitoQ and AntiOxCINs on RLM respiration supported by 5 mM succinate. (A) Effects of MitoQ (white, control; horizontal pattern, 2.5 µM, vertical pattern, 5 µM); (B-H), Effects of AntiOxCINs (white, control; horizontal pattern, 2.5 µM, vertical pattern, 5 µM, checkered pattern, 10 µM). The statistical significance relative to the different respiratory rates/states was determined using Student's two tailed t-test.

In an embodiment, it was observed that MitoQ, for all tested concentrations, caused a significant decrease of RCR and ADP/O parameters. (Table 2). Moreover, when RLM were incubated with MitoQ concentrations up to 5 µM an increase on state 2, state 4 and oligomycin-inhibited respiration and a decrease on state 3 and FCCP-uncoupled respiration, using glutamate/malate as substrate was observed (FIG. 6A). When using succinate, RLM were completely uncoupled in the presence of MitoQ at the highest concentration tested (FIG. 6A). The incubation with increasing concentrations of MitoQ resulted in a progressive decrease of the maximum $\Delta\Psi$ obtained upon energization (Table 2). MitoQ (5 µM) also decreased the ability of $\Delta\Psi$ mitochondria to recover to a value similar to the control. $\Delta\Psi$ collapse after ADP addition was observed with 10 µM MitoQ, since no repolarization occurred after ADP-induced depolarization (Table 2).

In an embodiment, the highest concentration used in AntiOxCINs toxicity studies was the one in which MitoQ completely disrupted mitochondrial bioenergetics. The data of AntiOxCINs toxicity studies were shown in Tables 3 to 9. AntiOxCIN$_1$ was also included in the mentioned studies for comparative analysis (Table 3).

TABLE 3

Effect of AntiOxCIN$_1$ on mitochondrial bioenergetics: mitochondrial respiratory control ratio (RCR), efficiency of the phosphorylative system (ADP/O), and mitochondrial transmembrane potential ($\Delta\Psi$).

| | Mitochondrial Bioenergetics | Control | AntiOxCIN$_1$ 2.5 µM | AntiOxCIN$_1$ 5 µM | AntiOxCIN$_1$ 10 µM |
|---|---|---|---|---|---|
| Glutamate/Malate | Maximum potential ($\Delta\Psi$ in - mV) | 225.8 ± 9.8 | 208.7 ± 9.5 | 210.6 ± 11.4 | 213.9 ± 10.7 |
| | ADP-induced depolarization ($\Delta\Psi$ in - mV) | 194.2 ± 7.9 | 184.2 ± 8.2 | 187.1 ± 10.3 | 187.4 ± 9.2 |
| | Repolarization Potential ($\Delta\Psi$ in - mV) | 223.0 ± 9.7 | 208.0 ± 9.4 | 209.8 ± 11.1 | 209.1 ± 9.7 |
| | Lag Phase (s) | 70.7 ± 6.0 | 84.7 ± 6.6 | 72.0 ± 2.1 | 87.7 ± 5.1 |
| | RCR | 6.4 ± 0.6 | 5.4 ± 0.6 | 5.1 ± 0.7 | 4.4 ± 0.2 * |
| | ADP/O | 2.6 ± 0.1 | 2.5 ± 0.1 | 2.4 ± 0.1 | 2.3 ± 0.1 |
| Succinate | Maximum potential ($\Delta\Psi$ in - mV) | 202.1 ± 6.7 | 194.7 ± 3.6 | 195.8 ± 8.8 | 195.2 ± 4.5 |
| | ADP-induced depolarization ($\Delta\Psi$ in - mV) | 173.9 ± 5.3 | 172.2 ± 3.9 | 173.3 ± 6.4 | 175.2 ± 5.7 |
| | Repolarization Potential ($\Delta\Psi$ in - mV) | 195.9 ± 5.5 | 195.9 ± 4.7 | 194.3 ± 11.8 | 195.3 ± 8.3 |
| | Lag Phase (s) | 106.0 ± 12.4 | 100.6 ± 12.8 | 121.6 ± 15.0 | 132.6 ± 30.4 |
| | RCR | 4.9 ± 0.7 | 3.5 ± 0.3 | 3.3 ± 0.5 | 3.2 ± 0.2 |
| | ADP/O | 1.6 ± 0.1 | 1.4 ± 0.1 | 1.3 ± 0.1 | 1.4 ± 0.1 |

*, , * Statistically significant compared with control using Student's two tailed t-test.

TABLE 4

Effect of AntiOxClN$_2$ on mitochondrial bioenergetics: mitochondrial respiratory control ratio (RCR), efficiency of the phosphorylative system (ADP/O), and mitochondrial transmembrane potential ($\Delta\Psi$).

| | | | AntiOxClN$_2$ | | |
| --- | --- | --- | --- | --- | --- |
| Mitochondrial Bioenergetics | | Control | 2.5 µM | 5 µM | 10 µM |
| Glutamate/Malate | Maximum potential ($\Delta\Psi$ in - mV) | 225.8 ± 9.8 | 208.4 ± 10.1 | 214.8 ± 11.7 | 209.8 ± 9.4 |
| | ADP-induced depolarization ($\Delta\Psi$ in - mV) | 194.2 ± 7.9 | 186.2 ± 8.9 | 199.2 ± 13.3 | 193.3 ± 9.1 |
| | Repolarization Potential ($\Delta\Psi$ in - mV) | 223.0 ± 9.7 | 205.1 ± 9.0 | 214.0 ± 12.5 | 202.0 ± 8.0 |
| | Lag Phase (s) | 70.7 ± 6.0 | 81.2 ± 7.2 | 79.5 ± 7.0 | 88.7 ± 25.1 |
| | RCR | 6.4 ± 0.6 | 5.2 ± 1.0 | 3.9 ± 0.6 * | 3.4 ± 0.3 ** |
| | ADP/O | 2.6 ± 0.1 | 2.4 ± 0.04 | 2.2 ± 0.1 * | 2.2 ± 0.1 * |
| Succinate | Maximum potential ($\Delta\Psi$ in - mV) | 202.1 ± 6.7 | 190.5 ± 5.9 | 189.7 ± 8.0 | 190.0 ± 6.3 |
| | ADP-induced depolarization ($\Delta\Psi$ in - mV) | 173.9 ± 5.3 | 169.3 ± 4.0 | 174.9 ± 5.5 | 178.7 ± 6.3 |
| | Repolarization Potential ($\Delta\Psi$ in - mV) | 195.9 ± 5.5 | 191.5 ± 7.5 | 189.5 ± 9.0 | 186.6 ± 7.1 |
| | Lag Phase (s) | 106.0 ± 12.4 | 101.2 ± 7.5 | 64.6 ± 19.4 | 46.2 ± 12.4 * |
| | RCR | 4.9 ± 0.7 | 3.3 ± 0.2 | 3.3 ± 0.2 | 2.1 ± 0.2 *** |
| | ADP/O | 1.6 ± 0.1 | 1.4 ± 0.1 | 1.3 ± 0.1 | 1.1 ± 0.1 ** |

*, , * Statistically significant compared with control using Student's two tailed t-test.

TABLE 5

Effect of AntiOxClN$_3$ on mitochondrial bioenergetics: mitochondrial respiratory control ratio (RCR), efficiency of the phosphorylative system (ADP/O), and mitochondrial transmembrane potential ($\Delta\Psi$).

| | | | AntiOxClN$_3$ | | |
| --- | --- | --- | --- | --- | --- |
| Mitochondrial Bioenergetics | | Control | 2.5 µM | 5 µM | 10 µM |
| Glutamate/Malate | Maximum potential ($\Delta\Psi$ in - mV) | 225.8 ± 9.8 | 238.0 ± 9.8 | 238.9 ± 8.6 | 238.0 ± 6.7 |
| | ADP-induced depolarization ($\Delta\Psi$ in - mV) | 194.2 ± 7.9 | 199.4 ± 7.4 | 200.7 ± 5.5 | 302.5 ± 6.3 |
| | Repolarization Potential ($\Delta\Psi$ in - mV) | 223.0 ± 9.7 | 234.8 ± 10.3 | 235.0 ± 8.4 | 231.5 ± 7.2 |
| | Lag Phase (s) | 70.7 ± 6.0 | 65.8 ± 6.6 | 68.2 ± 9.6 | 73.8 ± 12.1 |
| | RCR | 6.4 ± 0.6 | 3.8 ± 0.5 * | 3.5 ± 0.5 ** | 3.3 ± 0.3 ** |
| | ADP/O | 2.6 ± 0.1 | 2.4 ± 0.2 | 2.7 ± 0.2 | 2.4 ± 0.1 |
| Succinate | Maximum potential ($\Delta\Psi$ in - mV) | 202.1 ± 6.7 | 191.2 ± 9.1 | 193.3 ± 7.6 | 189.7 ± 7.8 |
| | ADP-induced depolarization ($\Delta\Psi$ in - mV) | 173.9 ± 5.3 | 171.5 ± 7.3 | 174.5 ± 7.7 | 172.2 ± 7.5 |
| | Repolarization Potential ($\Delta\Psi$ in - mV) | 195.9 ± 5.5 | 186.7 ± 9.3 | 190.4 ± 8.3 | 184.2 ± 7.6 |
| | Lag Phase (s) | 106.0 ± 12.4 | 84.6 ± 16.7 | 92.0 ± 10.3 | 79.8 ± 17.6 |
| | RCR | 4.9 ± 0.7 | 4.1 ± 0.5 | 4.7 ± 0.7 | 3.9 ± 0.6 |
| | ADP/O | 1.6 ± 0.1 | 1.6 ± 0.1 | 1.8 ± 0.3 | 1.6 ± 0.1 |

*, ** Statistically significant compared with control using Student's two tailed t-test.

TABLE 6

Effect of AntiOxClN$_6$ on mitochondrial bioenergetics: mitochondrial respiratory control ratio (RCR), efficiency of the phosphorylative system (ADP/O), and mitochondrial transmembrane potential ($\Delta\Psi$).

| | | | AntiOxClN$_6$ | | |
| --- | --- | --- | --- | --- | --- |
| Mitochondrial Bioenergetics | | Control | 2.5 µM | 5 µM | 10 µM |
| Glutamate/Malate | Maximum potential ($\Delta\Psi$ in - mV) | 225.8 ± 9.8 | 237.9 ± 5.9 | 227.5 ± 6.5 | 200.5 ± 16.80 |
| | ADP-induced depolarization ($\Delta\Psi$ in - mV) | 194.2 ± 7.9 | 202.5 ± 5.7 | 197.9 ± 5.0 | 174.2 ± 16.8 |

TABLE 6-continued

Effect of AntiOxClN$_6$ on mitochondrial bioenergetics: mitochondrial respiratory control ratio (RCR), efficiency of the phosphorylative system (ADP/O), and mitochondrial transmembrane potential ($\Delta\Psi$).

|  | Mitochondrial Bioenergetics | Control | AntiOxClN$_6$ 2.5 µM | 5 µM | 10 µM |
|---|---|---|---|---|---|
|  | Repolarization Potential ($\Delta\Psi$ in - mV) | 223.0 ± 9.7 | 233.3 ± 6.5 | 220.7 ± 6.2 | 185.3 ± 20.8 |
|  | Lag Phase (s) | 70.7 ± 6.0 | 73.2 ± 8.8 | 75.2 ± 12.5 | 47.8 ± 8.7 * |
|  | RCR | 6.4 ± 0.6 | 3.1 ± 0.3 *** | 3.3 ± 0.2 ** | 2.6 ± 0.1 *** |
|  | ADP/O | 2.6 ± 0.1 | 2.5 ± 0.1 | 2.5 ± 0.2 | 2.3 ± 0.1 |
| Succinate | Maximum potential ($\Delta\Psi$ in - mV) | 202.1 ± 6.7 | 181.9 ± 6.2 | 178.3 ± 4.7 * | 151.7 ± 9.3 *** |
|  | ADP-induced depolarization ($\Delta\Psi$ in - mV) | 173.9 ± 5.3 | 166.8 ± 6.1 | 167.1 ± 5.7 | 143.6 ± 11.0 * |
|  | Repolarization Potential ($\Delta\Psi$ in - mV) | 195.9 ± 5.5 | 177.7 ± 4.5 | 178.1 ± 5.1 | 149.0 ± 11.2 *** |
|  | Lag Phase (s) | 106.0 ± 12.4 | 77.8 ± 11.2 | 83.4 ± 11.5 | 62.2 ± 11.2 |
|  | RCR | 4.9 ± 0.7 | 3.7 ± 0.6 | 3.2 ± 0.3 | 2.6 ± 0.3 * |
|  | ADP/O | 1.6 ± 0.1 | 1.5 ± 0.1 | 1.5 ± 0.1 | 1.6 ± 0.11 |

*, , * Statistically significant compared with control using Student's two tailed t-test.

TABLE 7

Effect of AntiOxClN$_4$ on mitochondrial bioenergetics: mitochondrial respiratory control ratio (RCR), efficiency of the phosphorylative system (ADP/O), and mitochondrial transmembrane potential ($\Delta\Psi$).

|  | Mitochondrial Bioenergetics | Control | AntiOxClN$_4$ 2.5 µM | 5 µM | 10 µM |
|---|---|---|---|---|---|
| Glutamate/ Malate | Maximum potential ($\Delta\Psi$ in - mV) | 225.8 ± 9.8 | 214.6 ± 10.9 | 216.4 ± 13.1 | 216.8 ± 15.7 |
|  | ADP-induced depolarization ($\Delta\Psi$ in - mV) | 194.2 ± 7.9 | 188.5 ± 9.6 | 193.8 ± 11.8 | 192.7 ± 14.4 |
|  | Repolarization Potential ($\Delta\Psi$ in - mV) | 223.0 ± 9.7 | 211.8 ± 10.1 | 216.1 ± 12.7 | 207.7 ± 15.6 |
|  | Lag Phase (s) | 70.7 ± 6.0 | 84.7 ± 7.0 | 81.7 ± 6.7 | 65.7 ± 15.1 |
|  | RCR | 6.4 ± 0.6 | 5.3 ± 0.8 | 4.3 ± 0.7 * | 3.5 ± 0.5 ** |
|  | ADP/O | 2.6 ± 0.1 | 2.4 ± 0.1 | 2.2 ± 0.1 * | 2.2 ± 0.1 ** |
| Succinate | Maximum potential ($\Delta\Psi$ in - mV) | 202.1 ± 6.7 | 192.0 ± 4.0 | 197.6 ± 6.1 | 187.4 ± 8.5 |
|  | ADP-induced depolarization ($\Delta\Psi$ in - mV) | 173.9 ± 5.3 | 171.2 ± 3.7 | 176.2 ± 5.0 | 170.3 ± 5.2 |
|  | Repolarization Potential ($\Delta\Psi$ in - mV) | 195.9 ± 5.5 | 192.7 ± 5.4 | 195.4 ± 8.2 | 183.5 ± 10.5 |
|  | Lag Phase (s) | 106.0 ± 12.4 | 95.6 ± 7.5 | 97.8 ± 18.8 | 101.4 ± 23.75 |
|  | RCR | 4.9 ± 0.7 | 3.4 ± 0.3 | 3.0 ± 0.34 | 2.7 ± 0.4 * |
|  | ADP/O | 1.6 ± 0.1 | 1.4 ± 0.1 | 1.3 ± 0.1 | 1.3 ± 0.02 * |

*, ** Statistically significant compared with control using Student's two tailed t-test.

TABLE 8

Effect of AntiOxClN$_5$ on mitochondrial bioenergetics: mitochondrial respiratory control ratio (RCR), efficiency of the phosphorylative system (ADP/O), and mitochondrial transmembrane potential ($\Delta\Psi$).

|  | Mitochondrial Bioenergetics | Control | AntiOxClN$_5$ 2.5 µM | 5 µM | 10 µM |
|---|---|---|---|---|---|
| Glutamate/ Malate | Maximum potential ($\Delta\Psi$ in - mV) | 225.8 ± 9.8 | 249.8 ± 5.4 | 244.7 ± 7.0 | 215.1 ± 22.3 |
|  | ADP-induced depolarization ($\Delta\Psi$ in - mV) | 194.2 ± 7.9 | 207.5 ± 6.1 | 207.5 ± 5.6 | 184.6 ± 18.7 |
|  | Repolarization Potential ($\Delta\Psi$ in - mV) | 223.0 ± 9.7 | 244.7 ± 5.9 | 236.5 ± 6.8 | 199.9 ± 26.0 |
|  | Lag Phase (s) | 70.7 ± 6.0 | 74.4 ± 10.7 | 69.8 ± 13.3 | 53.2 ± 7.6 |
|  | RCR | 6.4 ± 0.6 | 3.7 ± 0.4 ** | 3.7 ± 0.4 ** | 3.2 ± 0.1 ** |
|  | ADP/O | 2.6 ± 0.1 | 2.4 ± 0.1 | 2.5 ± 0.1 | 2.5 ± 0.1 |

TABLE 8-continued

Effect of AntiOxCIN$_5$ on mitochondrial bioenergetics: mitochondrial respiratory control ratio (RCR), efficiency of the phosphorylative system (ADP/O), and mitochondrial transmembrane potential ($\Delta\Psi$).

| Mitochondrial Bioenergetics | | Control | AntiOxCIN$_5$ 2.5 µM | AntiOxCIN$_5$ 5 µM | AntiOxCIN$_5$ 10 µM |
|---|---|---|---|---|---|
| Succinate | Maximum potential ($\Delta\Psi$ in - mV) | 202.1 ± 6.7 | 196.2 ± 8.6 | 190.1 ± 6.8 | 180.8 ± 4.0 |
| | ADP-induced depolarization ($\Delta\Psi$ in - mV) | 173.9 ± 5.3 | 177.2 ± 7.7 | 173.6 ± 6.8 | 162.2 ± 7.7 |
| | Repolarization Potential ($\Delta\Psi$ in - mV) | 195.9 ± 5.5 | 190.6 ± 7.8 | 184.0 ± 7.1 | 168.4 ± 9.3 * |
| | Lag Phase (s) | 106.0 ± 12.4 | 80.2 ± 11.8 | 67.2 ± 13.4 | 58.4 ± 10.2 * |
| | RCR | 4.9 ± 0.7 | 4.2 ± 0.4 | 4.4 ± 0.8 | 4.0 ± 0.8 |
| | ADP/O | 1.6 ± 0.1 | 1.6 ± 0.1 | 1.5 ± 0.1 | 1.6 ± 0.1 |

*, ** Statistically significant compared with control using Student's two tailed t-test.

TABLE 9

Effect of AntiOxCIN$_7$ on mitochondrial bioenergetics: mitochondrial respiratory control ratio (RCR), efficiency of the phosphorylative system (ADP/O), and mitochondrial transmembrane potential ($\Delta\Psi$).

| Mitochondrial Bioenergetics | | Control | AntiOxCIN$_7$ 2.5 µM | AntiOxCIN$_7$ 5 µM | AntiOxCIN$_7$ 10 µM |
|---|---|---|---|---|---|
| Glutamate/Malate | Maximum potential ($\Delta\Psi$ in - mV) | 225.8 ± 9.8 | 251.8 ± 8.7 | 248.1 ± 3.3 | 232.1 ± 9.2 |
| | ADP-induced depolarization ($\Delta\Psi$ in - mV) | 194.2 ± 7.9 | 212.2 ± 7.9 | 212.6 ± 3.2 | 197.1 ± 11.8 |
| | Repolarization Potential ($\Delta\Psi$ in - mV) | 223.0 ± 9.7 | 248.3 ± 8.3 | 243.5 ± 5.0 | 212.6 ± 18.4 |
| | Lag Phase (s) | 70.7 ± 6.0 | 73.4 ± 8.4 | 71.0 ± 10.7 | 58.6 ± 5.4 |
| | RCR | 6.4 ± 0.6 | 3.6 ± 0.2 ** | 3.5 ± 0.3 ** | 3.3 ± 0.3 ** |
| | ADP/O | 2.6 ± 0.1 | 2.8 ± 0.3 | 2.4 ± 0.1 | 2.6 ± 0.1 |
| Succinate | Maximum potential ($\Delta\Psi$ in - mV) | 202.1 ± 6.7 | 205.3 ± 7.3 | 191.1 ± 9.0 | 176.9 ± 3.1 * |
| | ADP-induced depolarization ($\Delta\Psi$ in - mV) | 173.9 ± 5.3 | 183.8 ± 6.0 | 176.2 ± 8.7 | 163.6 ± 3.2 |
| | Repolarization Potential ($\Delta\Psi$ in - mV) | 195.9 ± 5.5 | 199.4 ± 7.1 | 186.8 ± 7.5 | 171.0 ± 5.0 * |
| | Lag Phase (s) | 106.0 ± 12.4 | 80.0 ± 14.9 | 76.0 ± 9.6 | 65.0 ± 8.7 |
| | RCR | 4.9 ± 0.7 | 4.1 ± 0.4 | 3.1 ± 0.2 * | 3.7 ± 0.3 |
| | ADP/O | 1.6 ± 0.1 | 1.8 ± 0.2 | 1.8 ± 0.2 | 1.7 ± 0.2 |

*, ** Statistically significant compared with control using Student's two-tailed t-test.

In an embodiment, and as example, the AntiOxCINs and MitoQ rates for state 2, state 3, state 4, oligomycin-inhibited respiration and mitochondrial respiration assays, and succinate (was used as substrate FCCP-stimulated respiration) are shown in FIG. 6A-H.

In an embodiment, it was found that AntiOxCINs induced alterations on the respiratory chain in a dose-dependent manner. In general, AntiOxCINs increased state 2, state 4 and oligomycin-inhibited respiration at concentrations higher than 2.5 µM in a process that is mainly dependent on their lipophilicity and not relying on their aromatic pattern (catechol vs pyrogallol) (FIG. 6B-H). A dual dose-dependent effect on state 3 respiration was observed, with a decrease caused by the less lipophilic compounds (AntiOxCIN$_2$ and AntiOxCIN$_4$), and an increase with the more lipophilic AntiOxCINs (AntiOxCIN$_3$, AntiOxCIN$_6$, AntiOxCIN$_5$ and AntiOxCIN$_7$) for all tested concentrations (2.5-10 µM) (FIG. 6B-H).

In an embodiment, it was shown that AntiOxCINs induced dose-dependent alterations in the respiratory profile of isolated RLM. Probably some of the observed effects can result from a membrane permeabilization effect or a proton shuttling activity. This effect may lead to stimulation of non-phosphorylation respiration and to a small ALP depolarization. Consequently, for some AntiOxCINs the mitochondrial phosphorylative system, as assessed by the ADP/O ratio, was also affected. A dual dose-dependent effect on state 3 respiration was observed, with a decrease on that respiratory state caused by the less lipophilic compounds (AntiOxCIN$_2$ and AntiOxCIN$_4$), and relevant increase of state 3 respiration observed with the more lipophilic AntiOxCINs (AntiOxCIN$_3$, AntiOxCIN$_6$, AntiOxCIN$_5$ and AntiOxCIN$_7$) (FIG. 6).

In an embodiment, and as an example, the direct effects of AntiOxCINs on AT were measured (Tables 3-9). After AntiOxCINs addition, $\Delta\Psi$ alterations were found to be similar regardless of the substrate used. In general, AntiOxCINs caused a slight dose-dependent $\Delta\Psi$ depolarization although incubation of RLM with 2.5 µM AntiOxCIN$_3$ (Table 5) and AntiOxCIN$_6$ (Table 6) or AntiOxCIN$_5$ (Table 8) and AntiOxCIN$_7$ (Table 9) promoted an initial slight hyperpolarization of 10 or 25 mV, respectively. However, incubations with AntiOxCIN$_6$ (concentrations above 5 µM) (Table 6) and AntiOxCIN$_7$ (10 µM) resulted in a significant decrease of $\Delta\Psi$ in succinate-energized mitochondria.

In an embodiment a AntiOxCINs ranking toxicity hierarchy on the mitochondrial bioenergetics apparatus was established:
AntiOxCIN$_1$<AntiOxCIN$_2$<AntiOxCIN$_3$<AntiOxCIN$_6$ (catechol series); AntiOxCIN$_4$<AntiOxCIN$_5$<AntiOxCIN$_7$ (pyrogallol series).

In an embodiment, the AntiOxCINs mitochondrial toxicity observed at higher concentrations may be associated with the lipophilicity of the spacer and/or the presence of a TPP moiety and has little, if any, relation with their (catechol vs pyrogallol). In fact, caffeic acid showed low toxicity toward the mitochondrial bioenergetic apparatus. Still, the presence of the TPP cation and a lipophilic spacer is essential for an efficient and sometimes extensive mitochondrial accumulation.

In an embodiment, it was found that at higher concentrations, mitochondria-targeted antioxidants, AntiOxCINs and MitoQ, can disrupt mitochondrial respiration by causing damage in the inner mitochondrial membrane or by inhibiting the respiratory chain, ATP synthesis or export machinery.

In an embodiment, it must be stressed that MitoQ effectively inhibited lipid peroxidation in RLM at 5 µM (FIGS. 4 and 5) but caused toxicity on the mitochondrial bioenergetic apparatus of RLM at 2.5 µM (FIG. 6A and Table 2).

In an embodiment, it was concluded that a suitable lipophilic balance must be attained along the drug discovery optimization process to circumvent toxicity of mitochondriotropic antioxidants.

In an embodiment, it was concluded that for the AntiOxCINs under study RLM toxicity was detected at higher concentrations than the ones needed to exert antioxidant effect, independently of their mechanism.

In an embodiment, it was concluded that in general AntiOxCINs showed a better safety profile than MitoQ.

Figure 7A:
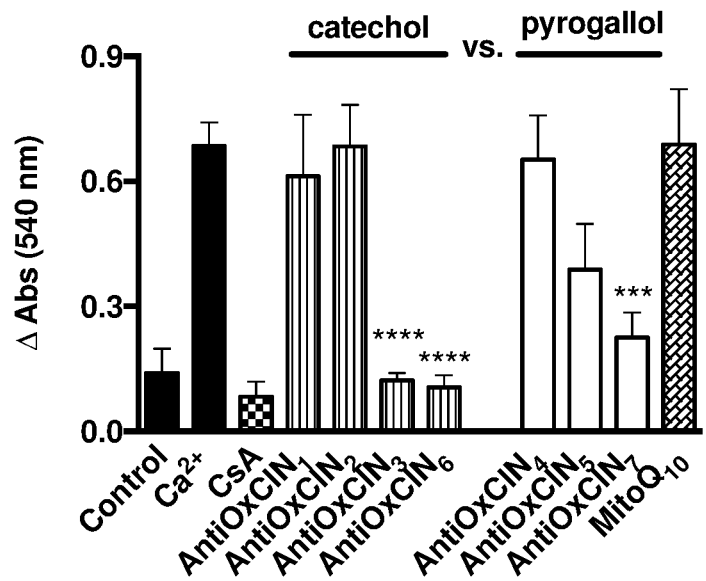
FIG. 7: Effect of AntiOxCINs and MitoQ on mitochondrial swelling upon induction of the mitochondrial permeability transition pore (mPTP). AntiOxCINs and MitoQ at (A) 2.5 µM, (B) 5 µM and (C) 10 µM were pre-incubated with RLM for 5 min before calcium addition. The comparisons were performed using one-way ANOVA between control ($Ca^{2+}$ only) vs. assays where AntiOxCIN derivatives were pre-incubated before $Ca^{2+}$. CsA-cyclosporin A
Figure 7B:
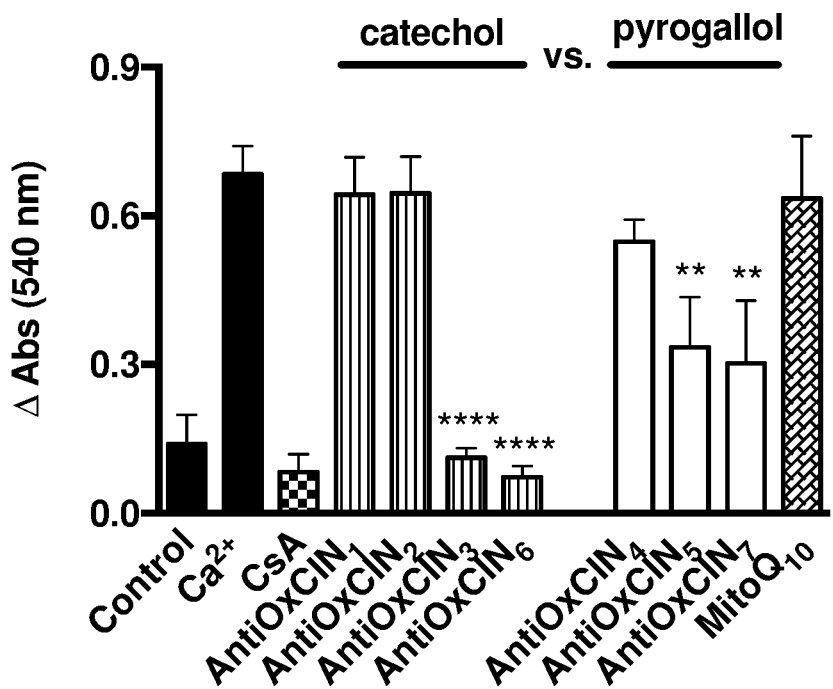
Figure 7C:
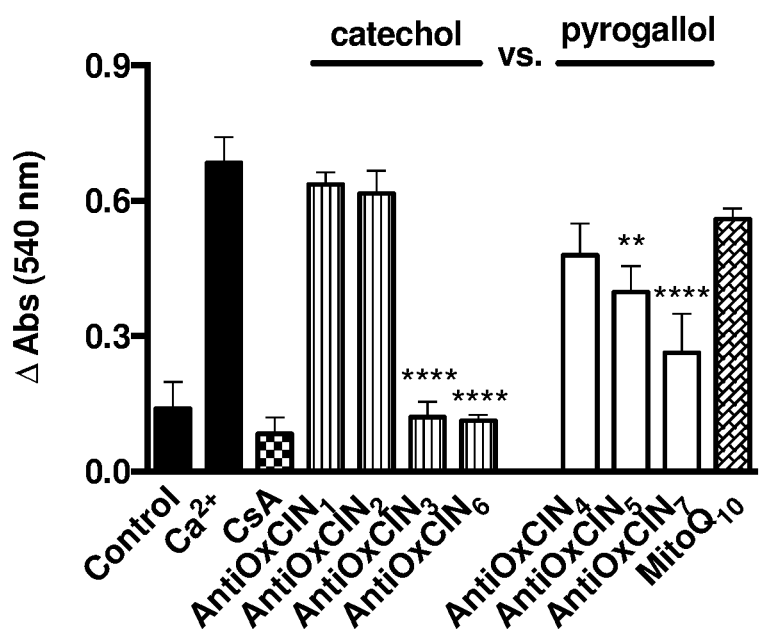

In an embodiment, the AntiOxCINs effects on mitochondrial permeability transition pore (mPTP) opening were evaluated. In general, less lipophilic AntiOxCINs had no effect on mPTP opening for all tested concentrations (FIG. 7A-C).

In an embodiment, it was found that the more lipophilic AntiOxCINs (AntiOxCIN$_3$, AntiOxCIN$_5$, AntiOxCIN$_6$, AntiOxCIN$_7$) caused an inhibition of calcium-dependent mPTP opening. For the catechol based compounds the effect was similar to that of cyclosporin A (1 µM), a classic mPTP desensitizer. MitoQ had no effect in mPTP induction (FIG. 7A-C). This property can be of therapeutic interest, for instance to prevent and treat graft-versus-host rejection in transplants, which normally involve mitochondrial disruption in the graft.

In an embodiment, and as an example, the cytotoxicity of two AntiOxCINs (AntiOxCIN$_4$ and AntiOxCIN$_6$) was assessed using monolayer cultures of human hepatocytes from hepatocellular carcinoma (HepG2) and SRB method (FIG. 8A). From the data, it was concluded that AntiOxCIN$_6$ (enfolding a catechol moiety) exhibited higher toxicity than AntiOxCIN$_4$ (harbouring a pyrogallol moiety) toward HepG2 cells (FIG. 6A). Remarkably, at concentrations higher than 2.5 µM AntiOxCIN$_6$ inhibited cell proliferation, while at concentrations higher than 100 µM AntiOxCIN$_4$ stimulated cell proliferation.

In an embodiment, it was concluded that AntiOxCIN$_6$ toxicity, based on its lipophilic properties (Table 1) and RLM accumulation rates (FIG. 3), can be mediated by other processes mediated by the presence of catechol redox chemistry, a property that is often linked to deleterious effects.

Figure 6B:
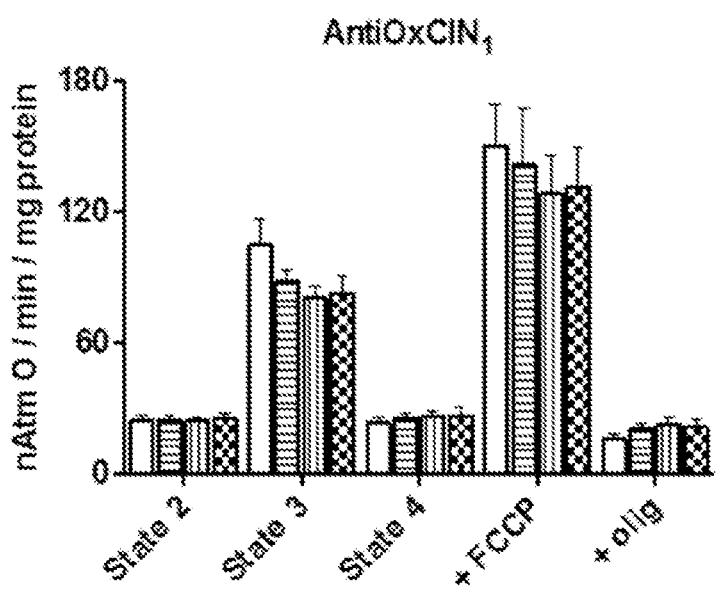
Figure 6C:
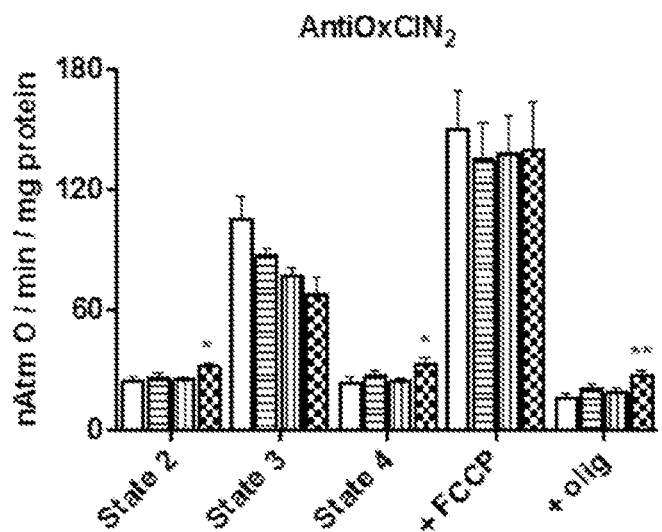
Figure 6D:
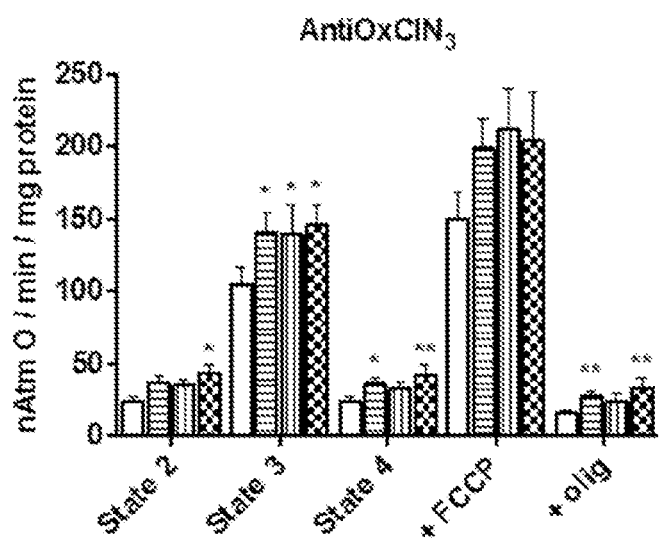
Figure 6E:
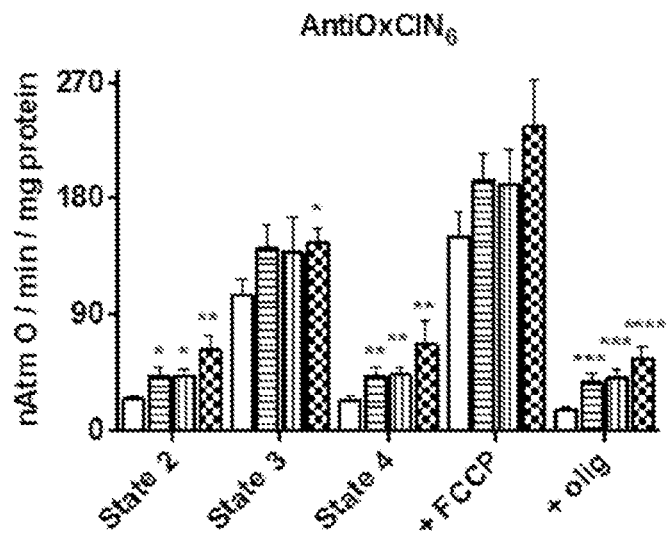
Figure 6F:
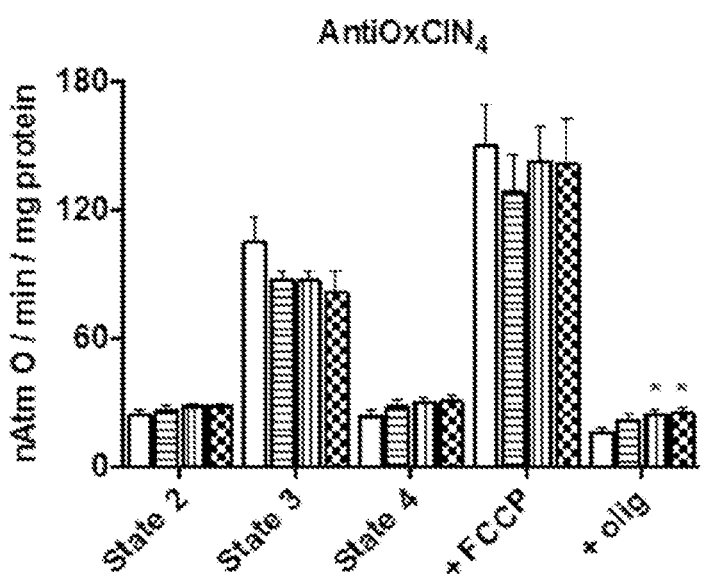
Figure 6G:
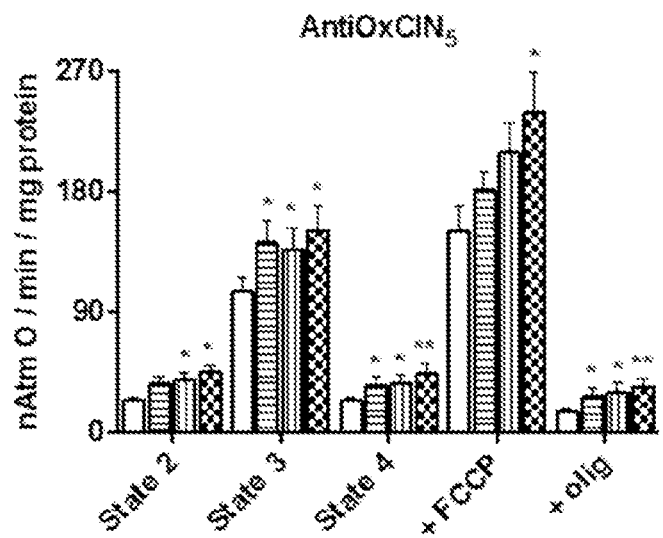
Figure 6H:
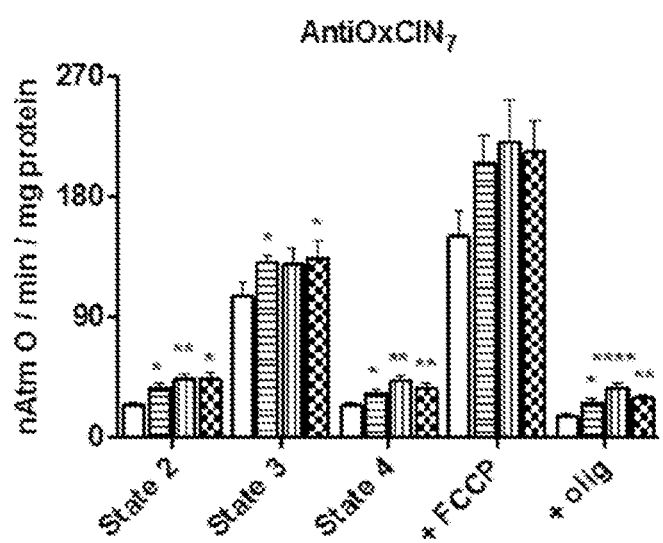

In an embodiment, as an example, the antioxidant cellular outline of AntiOxCIN$_4$ and AntiOxCIN$_6$ was assessed using monolayer cultures of human hepatocytes from hepatocellular carcinoma (HepG2) and two different oxidative stressors (250 µM FeSO$_4$ or 250 µM H$_2$O$_2$) (FIG. 8B). Both AntiOxCINs significantly prevented the iron- and hydrogen peroxide-induced HepG2 cytotoxicity, expressed as cell proliferation outcome (FIG. 6B). The higher efficacy of AntiOxCIN$_4$ is in agreement with the data attained from TAC assays (Table 1) and RLM assays (FIG. 4).

In an embodiment, as an example, the morphological changes in mitochondrial network and nuclei chromatin condensation of AntiOxCIN$_4$ and AntiOxCIN$_6$ have been determined. HepG2 cells were treated with AntiOxCINs for 48 h and then incubated with the mitochondrial $\Delta\Psi$-dependent fluorescent probes TMRM and DNA dye Hoechst 33342. The results showed that AntiOxCIN$_4$ (100 µM) and AntiOxCIN$_6$ (2.5 µM) did not induce nuclear morphological changes neither mitochondrial depolarization in HepG2 (FIG. 8C).

In an embodiment, it was concluded that the tailored structural modifications of AntiOxCIN$_1$ led to a significant improvement of its mitochondriotropic properties. Some AntiOxCINs have increased antioxidant activity, higher mitochondrial accumulation and lower toxicity.

In an embodiment, from AntiOxCINs series AntiOxCIN$_4$, a pyrogallol-based analogue, is predicted to be a potential candidate for development of a first class drugs with therapeutic application in mitochondrial oxidative-related disorders. AntiOxCIN$_4$ did not disturb mitochondrial morphology and polarization and showed a remarkable iron-chelation property not shared by MitoQ. AntiOxCIN$_4$ may be useful to mitigate the effects of mitochondrial iron overload and/or reduce mitochondrial iron stores in oxidative stress related diseases and conditions.

Examples of synthetic procedures followed to obtain and a number of intermediates and AntiOxCINs are provided.

In an embodiment, the structural characterization of the compounds was attained by spectrometric methods of analysis. $^1$H and $^{13}$C spectra NMR spectra were acquired at room temperature and recorded on a Bruker Avance III operating at 400 and 100 MHz, respectively. Chemical shifts are expressed in δ (ppm) values relative to tetramethylsilane (TMS) as internal reference and coupling constants (J) are given in Hz. Assignments were also made from DEPT (distortionless enhancement by polarization transfer) (underlined values). Mass spectra (MS) were recorded on a Bruker Microtof (ESI) or Varian 320-MS (EI) apparatus and referred in m/z (% relative) of important fragments.

In an embodiment, all the processes assisted by microwave were performed in a Biotage Initiator Microwave Synthesizer.

In an embodiment, the reaction progress was assessed by thin layer chromatography (TLC) analyses on aluminium silica gel sheets 60 F254 plates (Merck, Darmstadt, Germany) in dichloromethane, ethyl acetate and dichloromethane/methanol, in several proportions. The spots were detected using UV detection (254 and 366 nm). Flash column chromatography was performed using silica gel 60 (0.040-0.063 mm) (Carlo Erba Reactifs—SDS, France).

In an embodiment, the general synthetic procedure for obtention of cinnamic acid amides (compounds 3-8, FIG. 1) was as follows: 3,4-dimethoxycinnamic acid (1), or 3,4,5-trimethoxycinnamic acid (2), (1 mmol), was dissolved in dichloromethane (10 ml) and triethylamine (2 mmol). To the stirred solution, kept in an ice bath, ethyl chloroformate (2 mmol) was added dropwise. After stirring 2 hours at room temperature, the mixture was cooled in an ice bath and the pretended aminoalcohol (2 mmol) was added dropwise. The reaction was stirred during 10 hours at room temperature. After neutralization, the solvent was partially evaporated and the reactional mixture was extracted with dichloromethane (3×20 mL). The organic phases were combined, washed with water (3×20 mL), 10% aqueous sodium bicarbonate (NaHCO$_3$) (2×20 mL) and dried with anhydrous sodium sulphate (Na$_2$SO$_4$). After filtration, the solvent was evaporated and the pretended compound was obtained.

In an embodiment, the yield of (E)-3-(3,4-dimethoxyphenyl)-N-(6-hydroxyhexyl)prop-2-enamide (3) was 81%. The structural characterization of the compound was as follows: $^1$H (400 MHz, CDCl$_3$): δ=1.31 (4H, m, H3', H4'), 1.49 (4H, m, H2', H5'), 3.30 (2H, m, H1'), 3.55 (2H, t, J=6.5 Hz, H6'), 3.80 (3H, s, OCH$_3$), 3.81 (3H, s, OCH$_3$), 6.03 (1H, t, J=5.6 Hz, CONH), 6.25 (1H, d, J=15.5 Hz, Hα), 6.75 (1H, d, J=8.3 Hz, H5), 6.94 (1H, d, J=1.9 Hz, H2), 6.99 (1H, dd, J=1.7, 8.4 Hz, H6), 7.48 (1H, d, J=15.5 Hz, Hβ). $^{13}$C (100 MHz, CDCl$_3$): δ=25.4 (C3'), 26.6 (C4'), 30.0 (C2'), 32.7 (C5'), 39.7 (C1'), 56.0 (2×(OCH$_3$), 62.7 (C6'), 109.9 (C2), 111.2 (C5), 118.9 (Cα), 121.9 (C6), 128.0 (C1), 140.8 (Cβ), 149.2 (C4), 150.6 (C3), 166.5 (CONH). EI/ME m/z (%): 307 (M+, 17), 206 (62), 192 (27), 191 (100), 189 (29).

In an embodiment, the yield of (E)-3-(3,4,5-trimethoxyphenyl)-N-(6-hydroxyhexyl)prop-2-enamide (4) was 88%. The structural characterization of the compound was as follows: $^1$H (400 MHz, CDCl$_3$): δ=1.37 (4H, m, H3', H4'), 1.56 (4H, m, H2', H5'), 3.36 (2H, m, H1'), 3.62 (2H, t, J=6.6 Hz, H6'), 3.85 (6H, s, 2×OCH$_3$), 3.86 (3H, s, OCH$_3$), 6.35 (1H, t, J=5.6 Hz, CONH), 6.40 (1H, d, J=15.5 Hz, Hα), 6.72 (2H, s, H2, H6), 7.52 (1H, d, J=15.5 Hz, Hβ). $^{13}$C (100 MHz, CDCl$_3$): δ=25.1 (C3'), 26.2 (C4') 29.8 (C2'), 32.3 (C5'), 39.3 (C1'), 55.9 (2×OCH$_3$), 60.7 (OCH$_3$), 62.3 (C6'), 104.7 (C2, C6), 120.2 (Ca), 130.3 (C1), 139.2 (C4), 140.4 (Cβ), 153.1 (C3, C5), 166.0 (CONH). EI/ME m/z (%): 337 (M+, 64), 336 (41), 236 (27), 222 (58), 221 (100).

In an embodiment, the yield of (E)-3-(3,4-dimethoxyphenyl)-N-(8-hydroxyoctyl)prop-2-enamide (5) was 83%. The structural characterization of the compound was as follows: $^1$H (400 MHz, CDCl$_3$): δ=1.26-1.40 (6H, m, H3', H4', H5'), 1.51-1.62 (4H, m, H2', H6'), 1.70-1.81 (2H, m, H7'), 3.37 (2H, dd, J=7.0, 13.0 Hz, H1'), 3.63 (2H, t, J=6.6 Hz, H8'), 3.89 (3H, s, OCH$_3$), 3.89 (3H, s, OCH$_3$), 5.82 (1H, bs, CONH), 6.29 (1H, d, J=15.5 Hz, Ha), 6.84 (1H, d, J=8.3 Hz, H5), 7.02 (1H, d, J=1.9 Hz, H2), 7.07 (1H, dd, J=8.3, 1.9 Hz, H6), 7.55 (1H, d, J=15.5 Hz, Hβ). $^{13}$C (100 MHz, CDCl$_3$): δ=25.6 (C6'), 26.8 (C3'), 29.2 (C4'), 29.3 (C5'), 29.7 (C2'), 32.7 (C7'), 39.7 (C1'), 55.9 (OCH$_3$), 56.0 (OCH$_3$), 62.9 (C8'), 109.8 (C2), 111.1 (C5), 118.8 (C6), 121.9 (Ca), 127.9 (C1), 140.6 (Cβ), 149.1 (C4), 150.5 (C3), 166.2 (CONH). EI/ME m/z (%): 336 (M+1, 40), 335 (M+, 71), 206 (53), 192 (75), 191 (100), 151 (63).

In an embodiment, the (E)-3-(3,4,5-trimethoxyphenyl)-N-(8-hydroxyoctyl)prop-2-enamide (6) was yield: 89%. The structural characterization of the compound was as follows: $^1$H (400 MHz, CDCl$_3$): δ=1.28-1.41 (6H, m, H3', H4', H5') 1.44-1.70 (6H, m, H2', H6', H7'), 3.38 (2H, dd, J=7.0, 13.0 Hz, H1'), 3.64 (2H, t, J=6.6 Hz, H8'), 3.87 (3H, s, OCH$_3$), 3.88 (6H, s, 2×OCH$_3$), 5.67 (1H, t, J=7.0 Hz, CONH), 6.30 (1H, d, J=15.5 Hz, Hα) 6.73 (2H, s, J=6.7 Hz, H2, H6), 7.53 (1H, d, J=15.5 Hz, Hβ). $^{13}$C (100 MHz, CDCl$_3$): δ=25.6 (C6'), 26.8 (C3'), 29.2 (C4'), 29.3 (C5'), 29.7 (C2'), 32.7 (C7'), 39.8 (C1'), 56.2 (2×OCH$_3$), 61.0 (OCH$_3$), 63.0 (C8'), 105.0 (C2, C6), 120.2 (Cα), 130.5 (C1), 139.6 (C4), 140.8 (Cβ), 153.4 (C3, C5), 165.8 (CONH). EI/ME m/z (%): 366 (M+1, 39), 365 (M+, 98), 236. (45), 221 (100) 181 (37).

In an embodiment, the yield of (E)-3-(3,4-dimethoxyphenyl)-N-(10-hydroxydecyl)prop-2-enamide (7) was 78%. The structural characterization of the compound was as follows: $^1$H (400 MHz, CDCl$_3$): δ=1.21-1.41 (10H, m, H3', H4', H5', H6', H7'), 1.49-1.62 (4H, m, H2', H8'), 1.75-2.00 (2H, m, H9'), 3.32-3.42 (2H, m, H1'), 3.64 (2H, t, J=6.6 Hz, H10'), 3.90 (6H, s, 2×OCH$_3$), 5.79 (1H, bs, CONH), 6.29 (1H, d, J=15.5 Hz, Hα), 6.84 (1H, d, J=8.3 Hz, H5), 7.02 (1H, d, J=1.7 Hz, H2), 7.08 (1H, dd, J=8.3, 1.7 Hz, H6), 7.56 (1H, d, J=15.5 Hz, Hβ). $^{13}$C (100 MHz, CDCl$_3$): δ=25.8 (C8'), 27.0 (C3'), 29.3 (C4'), 29.45 (C5'), 29.49 (C6'), 29.6 (C7'), 29.8 (C2'), 32.9 (C9'), 39.9 (C1'), 56.0 (OCH$_3$), 56.1 (OCH$_3$), 63.2 (C101, 109.9 (C2), 111.3 (C5), 118.8 (C6), 122.0 (Cα), 128.0 (C1), 140.9 (Cβ), 149.3 (C4), 150.7 (C3), 166.3 (CONH). EI/ME m/z (%): 364 (M+1, 433), 363 (M+, 89), 206 (54), 192 (72), 191 (100), 151 (46).

In an embodiment, the yield of (E)-3-(3,4,5-trimethoxyphenyl)-N-(10-hydroxydecyl)prop-2-enamide (8) was 69%. The structural characterization of the compound was as follows: $^1$H (400 MHz, CDCl$_3$): δ=1.23-1.42 (10H, m, H3', H4', H5', H6', H7'), 1.51-1.61 (4H, m, H2', H8'), 1.89-2.06 (2H, m, H9'), 3.33-3.43 (2H, m, H1'), 3.64 (2H, t, J=6.6 Hz, H10'), 3.87 (3H, s, OCH$_3$), 3.88 (6H, s, 2×OCH$_3$), 5.82 (1H, bs, CONH), 6.33 (1H, d, J=15.6 Hz, Hα), 6.73 (2H, s, H2, H6), 7.55 (1H, d, J=15.5 Hz, Hp). 13c (100 MHz, CDCl$_3$): δ=25.8 (C8'), 27.0 (C3'), 29.3 (C4'), 29.45 (C5'), 29.50 (C6'), 29.6 (C7'), 29.8 (C2'), 32.9 (C9'), 39.9 (C1'), 56.0 (2×OCH$_3$), 61.1 (OCH$_3$), 63.2 (C101, 105.1 (C2, C6), 120.3 (Cα), 130.6 (C1), 139.7 (C4), 141.0 (Cβ), 153.5 (C3, C5), 165.9 (CONH). EI/ME m/z (%): 394 (M+1, 40), 393 (M+, 100), 236 (37) 222 (86), 221 (93).

In an embodiment, the synthetic procedure for obtention of methanesulfonates derivatives (compounds 9-14, FIG. 1) was as follows: the cinnamic acid amide (3-8) (1 mmol) was dissolved in a mixture of tetrahydrofuran (10 ml) and triethylamine (2 mmol) and stirred at room temperature over a period of 10 minutes. Then, a solution of methanesulfonyl chloride (1.3 mmol) in tetrahydrofuran (5 ml) was added dropwise. After stirring at room temperature for 12 hours, the mixture was neutralized and the solvent partially evaporated. The resulting reaction mixture was extracted with dichloromethane (3×20 mL) and the combined organic phases were washed with water (3×20 mL), 10% aqueous NaHCO$_3$ (2×20 mL), dried with anhydrous sodium sulphate (Na$_2$SO$_4$), filtered and evaporated. The crude product was used without further purification in the next step. A sample of each compound was purified and structural characterization was performed.

In an embodiment, the yield of (E)-(6-(3-(3,4-dimethoxyphenyl)prop-2-enamide)hexyl)methanesulfonate (9) was 87%. The structural characterization of the compound was as follows: The structural characterization of the compound was as follows: $^1$H (400 MHz, CDCl$_3$): δ=1.42 (4H, m, H3', H4'), 1.66 (4H, m, H2', H5'), 3.00 (3H, s, OSO$_2$CH$_3$), 3.38 (2H, m, H1'), 3.88 (3H, s, OCH$_3$), 3.89 (3H, s, OCH$_3$), 4.22 (2H, t, J=6.4 Hz, H6'), 5.97 (1H, t, J=5.6 Hz, CONH), 6.33 (1H, d, J=15.5 Hz, Hα), 6.84 (1H, d, J=8.3 Hz, H5), 7.03 (1H, d, J=1.9 Hz, H2), 7.07 (1H, dd, J=1.9, 8.3 Hz, H6), 7.55 (1H, d, J=15.5 Hz, H (3). $^{13}$C (100 MHz, CDCl$_3$): δ=24.9 (C3'), 26.0 (C4'), 28.8 (C2'), 29.3 (C5'), 37.2 (OSO$_2$CH$_3$), 39.2 (C1'), 55.7 (2×OCH$_3$), 69.8 (C6'), 109.5 (C2), 110.9 (C5), 118.6 (Cα), 121.7 (C6), 127.7 (C1), 140.4 (Cβ), 148.9 (C4), 150.3 (C3), 166.1 (CONH).

In an embodiment, the yield of (E)-(6-(3-(3,4,5-trimethoxyphenyl)prop-2-enamide)hexyl)methanesulfonate

(10) was 95%. The structural characterization of the compound was as follows: ¹H (400 MHz, CDCl₃): δ=1.36 (4H, m, H3', H4'), 1.60 (4H, m, H2', H5'), 2.95 (3H, s, OSO₂CH₃), 3.32 (2H, m, H1'), 3.80 (6H, s, 2×OCH₃), 3.81 (3H, s, OCH₃), 4.16 (2H, t, J=6.4 Hz, H6'), 6.07 (1H, t, J=5.7 Hz, CONH), 6.34 (1H, d, J=15.5 Hz, Hα), 6.68 (2H, s, H2, H6), 7.46 (1H, d, J=15.6 Hz, H (3). ¹³C (100 MHz, CDCl₃): δ=25.5 (C3'), 26.6 (C4'), 29.4 (C2'), 29.8 (C5'), 37.8 (OSO₂CH₃), 39.9 (C1'), 56.5 (2×OCH₃), 61.4 (OCH₃), 70.5 (C6'), 105.4 (C2, C6), 120.8 (Cα), 131.0 (C1), 139.8 (C4), 141.0 (Cβ), 154.8 (C3, C5), 166.4 (CONH).

In an embodiment, the yield of (E)-(8-(3-(3,4-dimethoxyphenyl)prop-2-enamide)octyl)methanesulfonate (11) was 95%. The structural characterization of the compound was as follows: ¹H (400 MHz, CDCl₃): δ=1.27-1.47 (8H, m, H3', H4', H5', H6'). 1.48-1.64 (2H, m, H2'), 1.66-1.79 (2H, m, H7'), 3.00 (3H, s, OSO₂CH₃), 3.37 (2H, dd, J=13.1-6.7 Hz, H1'), 3.88 (3H, s, OCH₃), 3.89 (3H, s, OCH₃), 4.21 (2H, t, J=6.5 Hz, H8'), 5.97 (1H, bs, CONH), 6.33 (1H, d, J=15.5 Hz, Hα), 6.83 (1H, d, J=8.3 Hz, H5), 7.03 (1H, s, H2), 7.07 (1H, d, J=8.1 Hz, H6), 7.55 (1H, d, J=15.5 Hz, H (3). ¹³C (100 MHz, CDCl₃): δ=25.3 (C6'), 26.7 (C3'), 28.8 (C4'), 29.00 (C5'), 29.05 (C2'), 29.6 (C7'), 37.4 (OSO₂CH₃), 39.7 (C1'), 55.87 (OCH₃), 55.95 (OCH₃), 70.2 (C8'), 109.7 (C2), 111.1 (C5), 118.9 (C6), 121.9 (Cα), 128.0 (C1), 140.5 (Cβ), 149.1 (C4), 150.5 (C3), 166.2 (CONH).

In an embodiment, the yield of (E)-(8-(3-(3,4,5-trimethoxyphenyl)prop-2-enamide)octyl)methanesulfonate (12) was 96%. The structural characterization of the compound was as follows: ¹H (400 MHz, CDCl₃): δ=1.29-1.45 (6H, m, H3', H4', H5'), 1.52-1.63 (4H, m, H2', H6'), 1.65-1.80 (2H, m, H7'), 3.00 (3H, s, OSO₂CH₃), 3.38 (2H, td, J=13.1, 7.0 Hz, H1'), 3.87 (3H, s, OCH₃), 3.88 (6H, s, 2×OCH₃), 4.23 (2H, t, J=6.5 Hz, H8'), 5.64 (1H, t, J=7.0 Hz, NH), 6.30 (1H, d, J=15.5 Hz, Hα), 6.73 (2H, s, H2, H6), 7.53 (1H, d, J=15.5 Hz, Hβ). ¹³C (100 MHz, CDCl₃): δ=25.3 (C6'), 26.7 (C3'), 28.8 (C7'), 29.0 (C4'), 29.1 (C5'), 29.6 (C2'), 37.4 (OSO₂CH₃), 39.7 (C1'), 56.2 (2×OCH₃), 61.0 (OCH₃), 70.1 (C8'), 105.0 (C2, C6), 120.1 (Cα), 130.5 (C1), 139.6 (C4), 140.8 (Cβ), 153.4 (C3, C5), 165.8 (CONH).

In an embodiment, the yield of (E)-(10-(3-(3,4-dimethoxyphenyl)prop-2-enamide)decyl)methanesulfonate (13) was 98%. The structural characterization of the compound was as follows: ¹H (400 MHz, CDCl₃): δ=1.20-1.45 (12H, m, H3', H4', H5', H6', H7', H8'), 1.49-1.64 (2H, m, H2'), 1.67-1.83 (2H, m, H9'), 3.01 (3H, s, OSO₂CH₃), 3.38 (2H, dd, J=10.9, 6.3 Hz, H1'), 3.90 (6H, s, 2×OCH₃), 4.23 (2H, t, J=6.6 Hz, H10'), 5.82-5.95 (1H, m, CONH), 6.32 (1H, d, J=15.5 Hz, Hα), 6.85 (1H, d, J=8.2 Hz, H5), 7.03 (1H, s, H2), 7.08 (1H, d, J=8.2 Hz, H6), 7.57 (1H, d, J=15.5 Hz, Hβ). ¹³C (100 MHz, CDCl₃): δ=25.4 (C8'), 27.0 (C3'), 29.0 (C5'), 29.2 (C4'), 29.28 (C6'), 29.34 (C7'), 29.4 (C2'), 29.8 (C9'), 37.5 (CH₃SO₃), 39.9 (C1'), 55.97 (OCH₃), 56.05 (OCH₃), 70.3 (C101, 109.8 (C2), 111.2 (C5), 118.8 (C6), 122.0 (Cα), 128.0 (C1), 140.8 (Cβ), 149.2 (C4), 150.6 (C3), 166.3 (CONH).

In an embodiment, the yield of (E)-(10-(3-(3,4,5-trimethoxyphenyl)prop-2-enamide)decyl)methanesulfonate (14) was 96%. The structural characterization was as follows: The structural characterization of the compound was as follows: ¹H (400 MHz, CDCl₃): δ=1.18-1.47 (12H, m, H3', H4', H5', H6', H7', H8'), 1.51-1.64 (2H, m, H2'), 1.68-1.82 (2H, m, H9'), 3.00 (3H, s, OSO₂CH₃), 3.32-3.45 (2H, m, H1'), 3.87 (3H, s, OCH₃), 3.88 (6H, s, 2×OCH₃), 4.22 (2H, t, J=6.6 Hz, H10'), 5.84 (1H, bs, CONH), 6.34 (1H, d, J=15.5 Hz, Hα), 6.74 (2H, s, H2, H6), 7.54 (1H, d, J=15.5 Hz, Hβ). ¹³C (100 MHz, CDCl₃): δ=25.5 (C8'), 27.0 (C3'), 29.0 (C51'), 29.0 (C4'), 29.2 (C6'), 29.3 (C7'), 29.35 (C2'), 29.40 (C9'), 37.5 (OSO₂CH₃), 40.0 (C1'), 56.3 (2×OCH₃), 60.1 (OCH₃), 70.3 (C10'), 105.2 (C2, C6), 105.2 (C6), 120.1 (Cα), 130.6 (C1), 139.8 (C4), 141.8 (Cβ), 153.6 (C3, C5), 166.1 (CONH).

In an embodiment, the synthetic procedures for obtention of cinnamic-based triphenylphosphonium salts (compounds 15-20, FIG. 1) by microwave or classic approaches is described.

In an embodiment, the obtention of triphenylphosphonium salts 15 and 16 was performed as follows: compound 9 or 10 (1 mmol) was thoroughly mixed with triphenylphosphine (1 mmol) in a microwave vial and sealed under argon. The reaction was placed under microwave irradiation at 150° C. for 1 hour and 30 minutes with magnetic stirring. Upon completion, the reaction mixture was cooled at room temperature and the crude product was purified by flash chromatography, using dichloromethane/methanol [9:1 ratio (v/v)] as elution system. The fractions containing the intended compound were combined and the solvent was evaporated. The resulting residue was then dissolved with a minimum amount of dichloromethane and triturated with excess ethyl ether. The solvent was decanted and the final solid residue was dried under vacuum to give the triphenylphosphonium methanesulfonate salt.

In an embodiment, the yield of (E)-(6-(3-(3,4-dimethoxyphenyl)prop-2-enamide)hexyl)triphenylphosphonium methanesulfonate (15) was 73%. The structural characterization of the compound was as follows: ¹H (400 MHz, CDCl₃): δ=1.38 (4H, m, H3', H4'), 1.47 (4H, m, H2', H5'), 3.17 (2H, d, J=5.1 Hz, H1'), 3.29 (2H, m, H6'), 3.69 (3H, s, OCH₃), 3.71 (3H, s, OCH₃), 6.62 (1H, d, J=8.3 Hz, H5), 6.82 (1H, d, J=15.7 Hz, Hα), 6.85 (1H, dd, J=1.9, 8.3 Hz, H6), 7.04 (1H, s, H2), 7.29 (1H, d, J=15.7 Hz, Hβ), 7.54-7.63 (15H, m, PPh₃), 8.30 (1H, t, J=5.3 Hz, CONH). ¹³C (100 MHz, CDCl₃): δ=21.2 (d, J_{CP}=51.8 Hz, C6'), 25.0 (C5') 28.1 (C4'), 28.9 (C3'), 38.2 (C2'), 39.0 (C1'), 55.4 (2×OCH₃), 109.2 (C2), 110.3 (C5), 117.5 (d, J_{CP}=85.9 Hz, C1"), 120.3 (Cα), 121.3 (C6), 128.1 (C1), 130.0 (d, J_{CP}=12.5 Hz, C3", C5"), 132.8 (d, J_{CP}=9.9 Hz, C2", C6"), 134.5 (d, J_{CP}=2.8 Hz, C4"), 138.0 (C (3), 148.4 (C4), 149.3 (C3), 166.4 (CONH). EM/IE m/z (%): 277 (25), 195 (33), 85 (85), 83 (100).

In an embodiment, the yield of (E)-(6-(3-(3,4,5-trimethoxyphenyl)prop-2-enamido)hexyl)triphenylphosphonium methanesulfonate (16) was 65%. The structural characterization of the compound was as follows: ¹H (400 MHz, DMSO): δ=1.33 (4H, m, H3', H4'), 1.52 (4H, m, H2', H5'), 3.15 (2H, m, H1'), 3.59 (2H, m, H6'), 3.69 (3H, s, OCH₃), 3.82 (6H, s, 2×OCH₃), 6.68 (1H, d, J=15.7 Hz, Hα), 6.90 (2H, s, H2, H6), 7.34 (1H, d, J=15.7 Hz, Hβ), 7.76-7.84 (15H, m, PPh₃), 8.18 (1H, t, J=5.6 Hz, CONH). ¹³C (100 MHz, DMSO): δ=20.2 (d, J_{CP}=49.7 Hz C6'), 21.8 (C5'), 25.6 (C4'), 28.8 (C3'), 29.6 (C2'), 38.5 (C1'), 55.9 (2×OCH₃), 60.2 (OCH₃), 104.9 (C2, C6), 118.6 (d, J_{CP}=85.7 Hz, C1"), 121.9 (Cα), 130.3 (d, J_{CP}=12.4 Hz, C3", C5"), 130.7 (C1), 133.6 (d, J_{CP}=10.1 Hz, C2", C6"), 134.9 (d, J_{CP}=2.4 Hz, C4"), 138.5 (C (3), 153.1 (C3, C5), 156.3 (C4), 165.0 (CONH). EM/IE m/z (%): 278 (24), 277 (48), 263 (34), 262 (100), 261 (22), 184 (22), 183 (75), 108 (38).

In an embodiment, the production of triphenylphosphonium salts 17-20 was performed as follows: methanesulfonate derivative (11-14) (1 mmol) was heated with triphenylphosphine (1 mmol) under argon atmosphere at 130° C. for 18 hours. The crude product was purified by flash chromatography, using dichloromethane/methanol [9:1 ratio (v/v)] as elution system. The fractions containing the pretended compound were combined and the solvent was evaporated. The resulting residue was then dissolved with a minimum amount of dichloromethane and triturated with excess ethyl ether. The solvent was decanted and the final solid residue was dried under vacuum to give the triphenylphosphonium methanesulfonate salt.

In an embodiment, the yield of (E)-(8-(3-(3,4-dimethoxyphenyl)acrylamido)octyl)triphenylphosphoniummethanesulfonate (17) was 53%. The structural characterization of the compound was as follows: $^1$H (400 MHz, MeOD): δ=1.25-1.40 (6H, m, H3', H4', H5'), 1.49-1.60 (4H, m, H2', H6'), 1.61-1.73 (2H, m, H7'), 2.68 (3H, s, OSO$_2$CH$_3$), 3.26 (2H, t, J=7.1 Hz, H1'), 3.43-3.33 (2H, m, H8'), 3.85 (3H, s, OCH$_3$), 3.86 (3H, s, OCH$_3$), 6.48 (1H, d, J=15.7 Hz, Hα), 6.96 (1H, d, J=8.3 Hz, H5), 7.11 (1H, dd, J=2.0, 8.3 Hz, H6), 7.15 (1H, d, J=2.0 Hz, H2), 7.44 (1H, d, J=15.7 Hz, Hβ), 7.70-7.94 (16H, m, PPh$_3$—CONH). $^{13}$C (100 MHz, MeOD): δ=22.6 (d, J$_{CP}$=51.2 Hz, C8'), 23.5 (d, J$_{CP}$=4.4 Hz, C6'), 27.7 (C3'), 29.7 (C4'), 29.9 (C5'), 30.4 (C2'), 31.4 (d, J$_{CP}$=16.0 Hz, C7'), 39.5 (OSO$_2$CH$_3$), 40.4 (C1'), 56.4 (OCH$_3$), 56.5 (OCH$_3$), 111.4 (C2), 112.8 (C5), 119.6 (C6), 120.0 (d, J$_{CP}$=85.8 Hz, C1''), 123.2 (Cα), 129.4 (C1), 131.5 (d, J$_{CP}$=12.6 Hz, C3'', C5''), 134.8 (d, J$_{CP}$=9.9 Hz, C2'', C6''), 136.3 (d, J$_{CP}$=3.0 Hz, C4''), 141.5 (Cβ), 150.7 (C4), 152.2 (C3), 168.9 (CONH). ME/ESI m/z (%): 581 (M++H–CH$_3$SO$_3$, 45), 580 (M$^+$—CH$_3$SO$_3$, 54), 462 (100).

In an embodiment, the yield of (E)-(8-(3-(3,4,5-trimethoxyphenyl)acrylamido)octyl)triphenylphosphonium methanesulfonate (18) was: 96%. The structural characterization of the compound was as follows: $^1$H (400 MHz, CDCl$_3$): δ=1.18-1.46 (6H, m, H3', H4', H5'), 1.51-1.66 (6H, m, H2', H6', H7'), 2.68 (3H, s, OSO$_2$CH$_3$), 3.33 (2H, dd, J=12.3-6.3 Hz, H1'), 3.58-3.43 (2H, m, H8'), 3.83 (3H, s, OCH$_3$), 3.85 (6H, s, 2×OCH$_3$), 6.85 (2H, s, H2, H6), 6.92 (1H, d, J=15.7 Hz, Hα), 7.46 (1H, d, J=15.6 Hz, Hβ), 7.62-7.85 (15H, m, PPh$_3$), 7.99 (1H, t, J=5.2 Hz, CONH). $^{13}$C (100 MHz, CDCl$_3$): δ=21.9 (d, J$_{CP}$=50.2 Hz, C8'), 22.3 (d, J$_{CP}$=4.5 Hz, C6'), 25.9 (C4'), 27.8 (C3'), 28.0 (C5'), 28.8 (C2'), 29.5 (d, J$_{CP}$=16.1 Hz, C7'), 39.3 (OSO$_2$CH$_3$), 39.7 (C1'), 56.3 (2×OCH$_3$), 60.9 (OCH$_3$), 105.1 (C2, C6), 118.5 (d, J$_{CP}$)=85.8 Hz, C1''), 122.4 (Cα), 130.5 (d, J$_{CP}$=12.5 Hz, C3'', C5''), 131.5 (C1), 133.5 (d, J$_{CP}$=9.9 Hz, C2'', C6''), 135.1 (d, J$_{CP}$=2.9 Hz, C4''), 138.8 (C4), 139.0 (Cβ), 153.2 (C3, C5), 166.7 (CONH). ME/ESI m/z (%): 611 (M++H—CH$_3$SO$_3$, 46) 610 (M$^+$—CH$_3$SO$_3$, 100).

In an embodiment, the yield of (E)-(10-(3-(3,4-dimethoxyphenyl)acrylamido)decyl)triphenylphosphonium methanesulfonate (19) was 61%. The structural characterization of the compound was as follows: $^1$H (400 MHz, MeOD): δ=1.18-1.41 (10H, m, H3', H4', H5', H6', H7'), 1.46-1.59 (4H, m, H2', H8'), 1.60-1.72 (2H, m, H9'), 2.68 (3H, s, OSO$_2$CH$_3$), 3.27 (2H, t, J=7.1 Hz, H1'), 3.32-3.42 (2H, m, H10'), 3.85 (3H, s, OCH$_3$), 3.86 (3H, s, OCH$_3$), 6.48 (1H, d, J=15.7 Hz, Hα), 6.95 (1H, d, J=8.2 Hz, H5), 7.11 (1H, dd, J=8.2, 1.9 Hz, H6), 7.14 (1H, d, J=1.9 Hz, H2), 7.44 (1H, d, J=15.7 Hz, Hβ), 7.95-7.68 (16H, m, PPh$_3$, CONH). $^{13}$C (100 MHz, MeOD): δ=22.6 (d, J$_{CP}$=51.1 Hz, C101, 23.5 (d, J$_{CP}$=4.5 Hz, C8'), 27.9 (C3'), 29.8 (C4'), 30.2 (C5', C6'), 30.35 (C7'), 30.42 (C2'), 31.5 (d, J$_{CP}$=16.1 Hz, C9'), 39.5 (OSO$_2$CH$_3$), 40.5 (C1'), 56.4 (OCH$_3$), 56.5 (OCH$_3$), 111.4 (C2), 112.8 (C5), 119.8 (C6), 120.0 (d, J$_{CP}$=85.8 Hz, C1''), 123.2 (Cα), 129.4 (C1), 131.5 (d, J$_{CP}$=12.5 Hz, C3'', C5''), 134.8 (d, J$_{CP}$)=9.9 Hz, C2'', C6''), 136.3 (d, J$_{CP}$=3.0 Hz, C4''), 141.5 (Cβ), 150.7 (C4), 152.2 (C3), 168.9 (CONH). ME/ESI m/z (%): 610 (M++H—CH$_3$SO$_3$, 73) 609 (M$^+$—CH$_3$SO$_3$, 100), 491 (33), 490 (67).

In an embodiment, the yield (E)-(10-(3-(3,4,5-trimethoxyphenyl)acrylamido)decyl)triphenylphosphonium methanesulfonate (20) was 69%. The structural characterization of the compound was as follows: $^1$H (400 MHz, MeOD): δ=1.20-1.41 (10H, m, H3', H4', H5', H6', H7'), 1.48-1.59 (4H, m, H2', H8'), 1.60-1.72 (2H, m, H9'), 2.68 (3H, s, OSO$_2$CH$_3$), 3.28 (2H, t, J=7.1 Hz, H1'), 3.35-3.45 (2H, m, H10'), 3.78 (3H, s, OCH$_3$), 3.86 (6H, s, 2×OCH$_3$), 6.55 (1H, d, J=15.7 Hz, Hα), 6.86 (2H, s, H2, H6), 7.43 (1H, d, J=15.7 Hz, Hβ), 7.70-7.96 (16H, m, PPh$_3$, CONH). $^{13}$C (100 MHz, MeOD): δ=22.6 (d, J$_{CP}$=51.0 Hz, C101, 23.5 (d, J$_{CP}$=4.4 Hz, C8'), 27.9 (C3'), 29.8 (C4'), 30.2 (C5', C6'), 30.37 (C7'), 30.42 (C2'), 31.5 (d, J$_{CP}$=16.0 Hz, C9'), 39.5 (OSO$_2$CH$_3$), 40.5 (C1'), 56.7 (2×OCH$_3$), 61.2 (OCH$_3$), 106.3 (C2, C6), 120.0 (d, J$_{CP}$=86.3 Hz, C1''), 121.5 (Cα), 132.2 (C1), 131.5 (d, J$_{CP}$=12.5 Hz, C3'', C5''), 134.8 (d, J$_{CP}$=10.0 Hz, C2'', C6''), 136.3 (d, J$_{CP}$=3.0 Hz, C4''), 140.7 (C4), 141.5 (Cβ), 154.8 (C3, C5), 168.6 (CONH). ME/ESI m/z (%): 640 (M++2–CH$_3$SO$_3$, 100), 639 (M++H–CH$_3$SO$_3$, 100), 418 (33).

In an embodiment, the general synthetic procedure for obtention of mitochondriotropic antioxidants (AntiOxCIN$_2$-AntiOxCIN$_2$, FIG. 1) was performed as follows: the triphenylphosphonium compound (15-20) (1 mmol) was dissolved in anhydrous dichloromethane (15 ml). The reaction mixture was stirred under argon and cooled at a temperature below −70° C. To this solution, boron tribromide (3 mmol, 1 M solution in dichloromethane) was added. Once the addition was completed, the reaction was kept at −70° C. for 10 minutes and then allowed to warm to the room temperature with continuous stirring for 12 hours. After BBr3 destruction with water, the purification process was carried out straightforward. After water removing the resulting product was dissolved in methanol and dried over anhydrous Na$_2$SO$_4$, filtered and the solvent evaporated.

In an embodiment, the yield of (E)-(6-(3-(3,4-dihydroxyphenyl)prop-2-enamido)hexyl)triphenylphosphonium methanesulfonate (AntiOxCIN$_2$) was 30%. The structural characterization of the compound was as follows: $^1$H (400 MHz, DMSO): δ=1.35 (4H, m, H3', H4'), 1.50 (4H, m, H2', H5'), 3.17 (2H, d, J=2.8 Hz, H1'), 3.58 (2H, m, H6'), 6.34 (1H, d, J=15.7 Hz, Hα), 6.75 (1H, d, J=8.0 Hz, H5), 6.82 (1H, dd, J=1.9, 8.0 Hz, H6), 6.94 (1H, d, J=1.9 Hz, H2), 7.20 (1H, d, J=15.7 Hz, Hβ), 7.74-7.92 (15H, m, PPh$_3$), 7.99 (1H, t, J=5.6 Hz, CONH), 9.14 (1H, s, OH), 9.39 (1H, s, OH). $^{13}$C (100 MHz, DMSO): δ=20.2 (d, J$_{CP}$=50.2 Hz, C6'), 21.8 (C5') 25.6 (C4'), 28.9 (C3'), 29.6 (C2'), 38.4 (C1'), 113.8 (C2), 115.8 (C5), 118.4 (d, J$_{CP}$)=85.6 Hz, C1''), 119.0 (Cα), 120.3 (C6), 126.4 (C1), 130.3 (d, J$_{CP}$=12.4 Hz, C3'', C5''), 133.6 (d, J$_{CP}$)=10.1 Hz, C2'', C6''), 134.9 (d, J$_{CP}$=2.4 Hz, C4''), 138.8 (Cβ), 145.5 (C4), 147.2 (C3), 165.3 (CONH). EM/IE m/z (%): 277 (25), 263 (33), 262 (100), 183 (74), 108 (34).

In an embodiment, the yield of (E)-(8-(3-(3,4-dihydroxyphenyl)acrylamido)octyl)triphenylphosphoniummethanesulfonate (AntiOxCIN$_3$) was 55%. The structural characterization of the compound was as follows: $^1$H (400 MHz, MeOD): δ=1.23-1.41 (6H, m, H3', H4', H5'), 1.47-1.59 (4H, m, H2', H6'), 1.60-1.73 (2H, m, H7'), 3.25 (2H, t, J=7.0 Hz, H1'), 3.33-3.44 (2H, m, H8'), 6.36 (1H, d, J=15.7 Hz, Hα), 6.75 (1H, d, J=8.2 Hz, H5), 6.87 (1H, dd, J=8.2, 2.0 Hz, H6), 6.99 (1H, d, J=2.0 Hz, H2), 7.36 (1H, d, J=15.7 Hz, Hβ), 7.68-7.94 (16H, m, PPh$_3$, CONH). $^{13}$C (100 MHz, MeOD): δ=22.7 (d, J$_{CP}$=51.0 Hz, C8'), 22.5 (d, J$_{CP}$=4.4 Hz, C6'), 27.7 (C3'), 29.7 (C4'), 29.9 (C5'), 30.4 (C2'), 31.4 (d, J$_{CP}$=16.0 Hz, C7'), 40.4 (C1'), 115.1 (C2), 116.5 (C5), 118.6 (C6), 120.0 (d, J$_{CP}$=86.3 Hz, C1''), 122.1 (Cα), 128.3 (C1), 131.6 (d, J$_{CP}$=12.6 Hz, C3'', C5''), 134.8 (d, J$_{CP}$=9.9 Hz, C2'', C6''), 136.3 (d, J$_{CP}$=3.0 Hz, C4''), 142.1 (Cβ), 146.8

(C4), 148.8 (C3), 169.2 (CONH). ESI/ME m/z (%): 553 (M++H–CH$_3$SO$_3$, 73), 552 (M–CH$_3$SO$_3$, 100), 462 (10).

In an embodiment, the yield of (E)-(10-(3-(3,4-dihydroxyphenyl)acrylamido)decyl)triphenylphosphonium methanesulfonate (AntiOxCIN$_6$) was 80%. The structural characterization of the compound was as follows: $^1$H (400 MHz, MeOD): δ=1.20-1.40 (10H, m, H3', H4', H5', H6', H7'), 1.47-1.57 (4H, m, H2', H8'), 1.59-1.71 (2H, m, H9'), 3.26 (2H, t, J=7.1 Hz, H1'), 3.33-3.41 (2H, m, H10'), 6.36 (1H, d, J=15.7 Hz, Hα), 6.75 (1H, d, J=8.2 Hz, H5), 6.88 (1H, dd, J=8.4, 2.1 Hz, H6), 6.99 (1H, d, J=2.1 Hz, H2), 7.36 (1H, d, J=15.7 Hz, Hβ), 7.68-7.98 (16H, m, PPh$_3$, CONH). $^{13}$C (100 MHz, MeOD): δ=22.7 (d, $J_{CP}$=51.0 Hz, C10), 23.5 (d, $J_{CP}$=4.4 Hz, C8'), 27.9 (C3'), 29.8 (C4'), 30.2 (C5', C6'), 30.3 (C7'), 30.4 (C2'), 31.5 (d, $J_{CP}$=16.1 Hz, C9'), 40.5 (C1'), 115.0 (C2), 116.5 (C5), 119.8 (C6), 120.0 (d, $J_{CP}$=86.3 Hz, C1"), 122.0 (Cα), 128.3 (C1), 131.5 (d, $J_{CP}$=12.6 Hz, C3", C5"), 134.8 (d, $J_{CP}$)=10.0 Hz, C2", C6"), 136.3 (d, $J_{CP}$=3.0 Hz, C4"), 142.0 (Cβ), 146.8 (C4), 148.7 (C3), 169.2 (CONH). ESI/ME m/z (%): 581 (M++H—CH$_3$SO$_3$, 85) 580 (M+—CH$_3$SO$_3$, 100), 490 (20).

In an embodiment, the yield of (E)-(6-(3-(3,4,5-trihydroxyphenyl)prop-2-enamido)hexyl)triphenylphosphonium methanesulfonate (AntiOxCIN$_4$) was 50%. The structural characterization of the compound was as follows: $^1$H (400 MHz, DMSO): δ=1.35 (4H, m, H3', H4'), 1.50 (4H, m, H2', H5), 2.72 (2H, m, H1'), 3.58 (2H, m, H6') 6.28 (1H, d, J=15.6 Hz, Hα), 6.47 (2H, s, H2, H6), 7.10 (1H, d, J=15.6 Hz, Hβ), 7.75-7.79 (15H, m, PPh$_3$), 8.00 (1H, t, J=5.6 Hz, CONH). $^{13}$C (100 MHz, DMSO): δ=19.8 (d, $J_{CP}$=49.5 Hz, C6'), 21.3 (C5'), 25.2 (C4'), 26.2 (C3'), 28.5 (C2'), 38.2 (C1'), 106.3 (C2, C6), 118.2 (d, $J_{CP}$=85.1 Hz, C1"), 118.6 (Cα), 124.9 (C1), 129.8 (d, $J_{CP}$=12.4 Hz, C3", C5"), 133.2 (d, $J_{CP}$=10.1 Hz, C2", C6"), 134.5 (d, $J_{CP}$=2.8 Hz, C4"), 134.7 (C4), 138.8 (Cβ), 145.7 (C3, C5), 164.9 (CONH). EM/IE m/z (%): 277 (40), 263 (26), 262 (100), 184 (20), 183 (78), 108 (36), 82 (76), 81 (33), 80 (78), 79 (35), 58 (22).

In an embodiment, the yield of (E)-(8-(3-(3,4,5-trihydroxyphenyl)acrylamido)octyl)triphenylphosphonium methanesulfonate (AntiOxCIN$_6$) was 88%. The structural characterization of the compound was as follows: $^1$H (400 MHz, MeOD): δ=1.25-1.42 (6H, m, H3', H4', H5'), 1.46-1.61 (4H, m, H2', H6'), 1.59-1.74 (2H, m, H7'), 3.24 (2H, t, J=7.0 Hz, H1'), 3.35 (3H, s, OSO$_2$CH$_3$), 3.43-3.32 (2H, m, H10'), 6.33 (1H, d, J=15.6 Hz, Hα), 6.56 (2H, s H2, H6), 7.28 (1H, d, J=15.6 Hz, Hβ), 7.70-7.92 (16H, m, PPh$_3$, CONH). $^{13}$C (100 MHz, MeOD): δ=22.7 (d, $J_{CP}$=51.1 Hz, C8'), 23.5 (d, $J_{CP}$=4.4 Hz, C6'), 27.7 (C3'), 29.7 (C4'), 29.9 (C5'), 30.3 (C2'), 31.4 (d, $J_{CP}$=16.1 Hz, C7'), 40.4 (C1', CH$_3$SO$_3$), 108.3 (C2, C6), 118.7 (Cα), 120.0 (d, $J_{CP}$=86.3 Hz, C1"), 127.4 (C1), 131.6 (d, $J_{CP}$=12.5 Hz, C3", C5"), 134.8 (d, $J_{CP}$=9.9 Hz, C2", C6"), 136.3 (d, $J_{CP}$=3.0 Hz, C4"), 126.8 (C4), 142.4 (Cβ), 147.2 (C3, C5), 169.2 (CONH). ESI/ME m/z (%): 569 (M++H—CH$_3$SO$_3$, 43), 568 (M+—CH$_3$SO$_3$, 100).

In an embodiment, the yield of (E)-(10-(3-(3,4,5-trihydroxyphenyl)acrylamido)decyl)triphenylphosphonium methanesulfonate (AntiOxCIN$_7$) was 53%. The structural characterization of the compound was as follows: $^1$H (400 MHz, MeOD): δ=1.19-1.43 (10H, m, H3', H4', H5', H6', H7'), 1.49-1.60 (4H, m, H2', H8'), 1.60-1.73 (2H, m, H9'), 3.28 (2H, t, J=7.0 Hz, H1'), 3.34-3.43 (2H, m, H10'), 6.34 (1H, d, J=15.6 Hz, Hα), 6.58 (2H, s, H2, H6), 7.31 (1H, d, J=15.6 Hz, Hβ), 7.71-7.95 (16H, m, PPh$_3$, CONH). $^{13}$C (100 MHz, MeOD): δ=22.7 (d, $J_{CP}$=51.0 Hz, C10'), 23.5 (d, $J_{CP}$=4.3 Hz, C8'), 27.9 (C3'), 29.8 (C4'), 30.2 (C5', C6'), 30.3 (C7'), 30.4 (C2'), 31.5 (d, $J_{CP}$=15.9 Hz, C9'), 40.5 (C1'), 108.2 (C2, C6), 118.7 (Cα), 120.0 (d, $J_{CP}$=86.3 Hz, C1"), 127.3 (C1), 131.5 (d, $J_{CP}$=12.5 Hz, C3", C5"), 134.8 (d, $J_{CP}$=9.9 Hz, C2", C6"), 136.3 (d, $J_{CP}$=3.0 Hz, C4"), 136.7 (C4), 142.4 (Cβ), 147.1 (C3, C5), 169.2 (CONH). ESI/ME m/z (%): 597 (M++H—CH$_3$SO$_3$, 67), 596 (M+—CH$_3$SO$_3$, 100) 418 (14).

The radical scavenging activity of AntiOxCINs was evaluated by means of total antioxidant capacity assays based on DPPH., ABTS.$^+$ and GO. radicals. All these methods involved the spectrophotometric measurement of the absorbance decrease resulting from radical (DPPH., ABTS.$^+$ or GO.) deactivation with an antioxidant. The results were expressed in IC$_{50}$, which is defined as the minimum antioxidant concentration necessary to reduce the amount of radical by 50%. Antioxidant assays were performed in a multiplate reader (Powerwave XS Microplate Reader) of Bio-Tech instruments.

In an embodiment, the DPPH. radical scavenging activity was performed as follows: solutions of the test compounds with increasing concentrations (range between 0 μM and 500 μM) were prepared in ethanol. A DPPH' ethanolic solution (6.85 mM) was also prepared and then diluted to reach the absorbance of 0.72±0.02 at 515 nm. Each compound solution (20 μL) was added to 180 μL of DPPH' solution in triplicate, and the absorbance at 515 nm was recorded minutely over 45 minutes. The percent inhibition of the radical was based on comparison between the blank (20 μL of ethanol and 180 μL of DPPH' solution), which corresponded to 100% of radical, and test compounds solutions. Dose-response curves were established for the determination of IC$_{50}$ values. Data are means±SEM of three independent experiments.

In an embodiment, the ABTS.$^+$ scavenging activity was evaluated as follows: ethanolic solutions of the test compounds with increasing concentrations (range between 10 μM and 500 μM) were prepared. ABTS.$^+$ radical cation solution was obtained by addition of 150 mM aqueous potassium persulfate solution (163 μL) to 10 mL of 7 mM aqueous ABTS solution followed by storage in the dark at room temperature for 16 h (2.45 mM final concentration). The solution was then diluted in ethanol to reach the absorbance of 0.72±0.02. After addition of the compound (20 μL), in triplicate, to ABTS.$^+$ solution (180 μL) the spectrophotometric measurement was carried out each minute over 15 minutes. The percent inhibition of radical was based on comparison between the blank (20 μL of ethanol and 180 μL of ABTS.$^+$ solution), which corresponds to 100% of radical, and test compounds solutions. Dose-response curves were established for the determination of IC$_{50}$ values. Data are means±SEM of three independent experiments.

In an embodiment, the GO' scavenging activity was evaluated as follows: solutions of test compounds with concentrations from 5 μM to 75 μM were prepared in ethanol. An ethanolic solution of 5 mM GO' was prepared and diluted to reach the absorbance of 1.00±0.02 at 428 nm. The addition (20 μL) in triplicate of compound solution to GO. solution (180 μL) was followed by absorbance measurement at 428 nm over 30 minutes, in the dark, at room temperature. The percent inhibition of radical was based on comparison between the blank (20 μL of ethanol and 180 μL of GO; solution), which corresponds to 100% of radical, and test compounds solutions. Dose-response curves were established for the determination of IC$_{50}$ values. Data are means±SEM of three independent experiments.

In an embodiment, the redox and lipophilic properties of AntiOxCINs were evaluated by electrochemical techniques.

In an embodiment, the electrochemical analytical data was obtained using a computer controlled potentiostat Autolab PGSTAT302N (Metrohm Autolab, Utrecht, Netherlands). Generally, cyclic voltammetry (CV) data was acquired at a scan rate of 50 mVs$^{-1}$. Differential pulse voltammetry (DPV) results were acquired at a step potential of 4 mV, pulse amplitude of 50 mV and scan rate of 8 mVs$^{-1}$. The electrochemical signals were monitored by the General Purpose Electrochemical System (GPES) version 4.9, software package. All electrochemical experiments were performed at room temperature in an electrochemical cell that was placed in a Faraday cage in order to minimize the contribution of background noise to the analytical signal.

In an embodiment, the process of evaluation of AntiOxCINs redox properties was conducted as follows: stock solutions of each compound (10 mM) were prepared by dissolving the appropriate amount in ethanol. The voltammetric working solutions were prepared in the electrochemical cell, at a final concentration of 0.1 mM. The pH 0.7.4 supporting electrolyte was prepared by diluting 6.2 mL of 0.2 M dipotassium hydrogen phosphate and 43.8 mL of 0.2 M potassium dihydrogen phosphate to 100 mL. Voltammetric data was acquired in a three-electrode system consisting of a glassy carbon electrode (GCE, d=2 mm) as working electrode, a counter electrode of platinum wire and a saturated Ag/AgCl reference electrode. In an embodiment, the evaluation of AntiOxCINs lipophilic properties was performed as follows: the electrochemical cell was a four-electrode system with arrays of micro liquid-liquid interfaces (μlTIES) containing two Ag/AgCl reference electrodes and two counter electrodes of Pt, one in each phase. The microporous membrane was sealed with a fluorosilicone sealant (Dow Corning 730) onto a glass cylinder which was filled with 4.0 mL of the aqueous phase, where the aliquots of AntiOxCINs solutions were added. The membrane was then immersed into the organic phase contained in the cell. The organic phase reference solution (a 2 mM BTPPACl+2 mM NaCl aqueous solution) was mechanically stabilized The aqueous supporting electrolyte solution was a Tris-HCl buffer 10 mM pH 7.0.

In an embodiment, AntiOxCINs iron chelating properties were evaluated by the spectrophotometric ferrozine method performed in a multiplate reader (Powerwave XS Microplate Reader) of Bio-Tech instruments.

In an embodiment, the AntiOxCINs iron chelating properties were evaluated as follows: in each well, a solution of the test compound (100 μM) and ammonium iron (II) sulphate in ammonium acetate (20 μM) were added, incubated for 10 min and the absorbance was read at 562 nm. Then, a freshly prepared solution of ferrozine (5 mM) was added to each well (96 μM final concentration). After a new incubation at 37° C. for 10 min period, the absorbance of [Fe(ferrozine)$_3$]$^{2+}$ complex was measured at 562 nm. Blank wells were run using DMSO instead of the test compounds. EDTA was used as a reference. All compounds were tested at a final concentration of 100 μM. The absorbance of the first reading was subtracted to the final values to abolish any absorbance due to the test compounds. Data are means±SEM of three independent experiments and are expressed as % of Fe(II) chelation (EDTA=100%).

In an embodiment, the evaluation of AntiOxCINs functional mitochondrial toxicity profile was performed in rat liver mitochondria (RLM). RLM were prepared by tissue homogenization followed by differential centrifugations in ice-cold buffer containing 250 mM sucrose, 10 mM HEPES (pH 7.4), 1 mM EGTA, and 0.1% fat-free bovine serum albumin. After obtaining a crude mitochondrial preparation, pellets were washed twice and resuspended in washing buffer (250 mM sucrose and 10 mM HEPES, pH 7.4). The protein concentration was determined by the biuret assay using BSA as a standard.

In an embodiment, the mitochondrial AntiOxCINs uptake was evaluated.

In an embodiment, the AntiOxCINs mitochondria uptake by energized RLM was evaluated as follows: RLM (0.5 mg protein/mL) were incubated with AntiOxCINs at 37° C. under constant stirring in 1 mL of KCl medium (120 mM KCl, 10 mM HEPES, pH 7.2 and 1 mM EGTA). Five sequential 1 μM additions of each AntiOxCINs were performed to calibrate the electrode response in the presence of rotenone (1.5 μM). Then, succinate (10 mM) was added to generate AN. Valinomicin (0.2 μg/mL) was added at the end of the assay to dissipate AN. The measurements were performed with an ion-selective electrode, which measure the distribution of tetraphenylphosphonium cation (TPP$^+$) and Ag/AgCl$_2$ electrode as reference. The mitochondrial accumulation ratio was calculated by the disappearance of AntiOxCINs from extra- to intramitochondrial medium assuming an intramitochondrial volume of 0.5 μL/mg protein and a binding correction for the mitochondrial uptake of TPP compounds.

The outcome of AntiOxCINs on RLM lipid peroxidation was evaluated. Two different methods have been used.

In an embodiment, the effect of AntiOxCINs on RLM lipid peroxidation was measured by thiobarbituric acid reactive species (TBARS) assay as follows: RLM (2 mg protein/ml) were incubated in 0.8 mL medium containing 100 mM KCl, 10 mM Tris-HCl and pH 7.6, at 37° C., supplemented with 5 mM glutamate/2.5 mM malate as substrate. RLM were incubated for 5 min period with each AntiOxCINs (5 μM) and then mitochondria were exposed to oxidative stress condition by the addition of 100 μM FeSO$_4$/500 μM H$_2$O$_2$/5 mM ascorbate for 15 min at 37° C. After exposure to oxidative stress, 60 μL of 2% (v/v) butylated hydroxytoluene in DMSO was added, followed by 200 μL of 35% (v/v) perchloric acid and 200 μL of 1% (w/v) thiobarbituric acid. Samples were then incubated for 15 min at 100° C., allowed to cool down and the supernatant transferred to a glass tube. After addition of 2 mL MiliQ water and 2 mL butan-1-ol, samples were vigorously vortexed for few seconds. The two phases were allowed to separate. The fluorescence of aliquots (250 μL) of the organic layer was analyzed in a plate reader ($\lambda_{Ex}$=515 nm; $\lambda_{Em}$=553 nm) for TBARS. The TBARS background production in RLM energized with glutamate/malate was found to be negligible. Data are means±SEM of three independent experiments and are expressed as % of control (control=100%).

In an embodiment, the effect of AntiOxCINs on RLM lipid peroxidation was measured by a second methodology as follows: the oxygen consumption of 2 mg RLM, in a total volume of 1 mL of a reaction medium consisting of 100 mM KCl, 10 mM Tris-HCl and pH 7.6, using glutamate/malate (5 mM/2.5 mM) as respiratory substrate, was monitored at 37° C. with a Clark oxygen electrode. RLM were incubated for 5 min period with each AntiOxCINs (5 μM) and then lipid peroxidation process started by adding 10 mM ADP and 0.1 mM FeSO$_4$ (final concentrations). The saturated concentration of O$_2$ in the incubation medium was assumed to be 217 μM at 37° C. Time-dependent changes on oxygen consumption resulting from peroxidation of RLM membranes by a pro-oxidant pair (1 mM ADP/0.1 mM FeSO$_4$) were recorded. The traces are means±SEM recording from six independent experiments. The time lag-phase associated with the slower oxygen consumption that followed the addition of ADP/$Fe^{2+}$ was used to measure the effectiveness of AntiOxCINs to prevent lipid peroxidation. Data are means±SEM from six independent experiments and are expressed as % of control (control=100%).

In an embodiment, the effect of AntiOxCINs on mitochondrial respiration was evaluated.

In an embodiment, the evaluation of AntiOxCINs effect on mitochondrial respiration was performed as follows: the respiration of isolated RLM was evaluated polarographically with a Clark-type oxygen electrode, connected to a suitable recorder in a 1 mL thermostated water-jacketed chamber with magnetic stirring, at 37° C.[1]. The standard respiratory medium consisted of 130 mM sucrose, 50 mM KCl, 5 mM $KH_2PO_4$, 5 mM HEPES (pH 7.3) and 10 μM EGTA. Increasing concentrations of AntiOxCINs (2.5-10 μM) were added to the reaction medium containing respiratory substrates glutamate/malate (10 mM and 5 mM respectively) or succinate (5 mM) and RLM (1 mg) and allowed to incubate for a 5 min period prior to the assay. State 2 was considered as the respiration during the 5 min incubation time with AntiOxCINs. To induce state 3 respiration, 125 nmol ADP (using glutamate/malate) or 75 nmol ADP (using succinate) was added. State 4 was determined after ADP phosphorylation finished. Subsequent addition of oligomycin (2 μg/ml) inhibited ATP-synthase and originated the oligomycin-inhibition respiration state. Finally, 1 μM FCCP was added to induce uncoupled respiration. The RCR was of 6.42±0.57 and 4.90±0.66 for the control experiments, with glutamate-malate or succinate as respiratory substrates, respectively. The ADP/O index was 2.64±0.10 and 1.58±0.09 with the same respiratory substrates, respectively Data are means are means±SEM of seven independent experiments.

In an embodiment, the effect of AntiOxCINs on transmembrane electric potential ($\Delta\Psi$) was evaluated.

In an embodiment, the evaluation of AntiOxCINs effect on mitochondrial transmembrane electric potential ($\Delta\Psi$) was performed as follows: the mitochondrial transmembrane electric potential ($\Delta\Psi$) was estimated through the evaluation of fluorescence changes of safranine (5 μM) and was recorded on a spectrofluorometer operating at excitation and emission wavelengths of 495 and 586 nm, with a slit width of 5 nm. Increasing concentrations of AntiOxCINs (2.5-10 μM) were added to the reaction medium (200 mM sucrose, 1 mM $KH_2PO_4$, 10 mM Tris (pH 7.4) and 10 μM EGTA) containing respiratory substrates glutamate/malate (5 mM and 2.5 mM respectively) or succinate (5 mM) and RLM (0.5 mg in 2 mL final volume) and allowed to incubate for a 5 min period prior to initiate the assay, at 25° C. In this assay, safranine (5 μM) and ADP (25 nmol) were used to initiate the assay and to induce depolarization, respectively. Then, 1 μM FCCP was added at the end of all experiments to depolarize mitochondria. $\Delta\Psi$ was calculated using a calibration curve obtained when RLM were incubated in a $K^+$-free reaction medium containing 200 mM sucrose, 1 mM $NaH_2PO_4$, 10 mM Tris (pH 7.4) and 10 μM EGTA, supplemented with 0.4 μg valinomicin. The extension of fluorescence changes of safranine induced by $\Delta\Psi$ was found to be similar in the standard and $K^+$-free medium. "Repolarization" corresponded to the recovery of membrane potential after the complete phosphorylation of ADP added. Lag phase reflected the time required to phosphorylate the added ADP. Isolated RLM developed a $\Delta\Psi\approx226$ mV and $\Delta\Psi\approx202$ mV (negative inside) when glutamate/malate or succinate were used, respectively. Data are means±SEM of five independent experiments.

In an embodiment, the effect of AntiOxCINs on mitochondrial permeability transition pore opening was evaluated.

In an embodiment, the effect of AntiOxCINs on mitochondrial permeability transition pore opening were measured as follows: mitochondrial swelling was estimated by measuring the alterations of light scattered from a mitochondrial suspension, as monitored spectrophotometrically at 540 nm. Increasing concentrations of AntiOxCINs (2.5-10 μM) were added to the reaction medium (200 mM sucrose, 1 mM $KH_2PO_4$, 10 mM Tris (pH 7.4), 5 mM succinate and 10 μM EGTA supplemented with 1.5 μM rotenone), in the presence of RLM (1 mg), and allowed to incubate for a 5 min period before the assay. The experiments were initiated by the addition of a suitable concentration of $Ca^{2+}$ (15-50 μM), titrated every day. Cyclosporin A (CsA), a PTP desensitizer, was added to demonstrate mPTP opening. The reaction was stirred continuously and the temperature maintained at 37° C. Data are means±SEM of three independent experiments and are expressed as Aabsorbance at 540 nm.

In an embodiment, the cytotoxicity profile of $AntiOxCIN_4$ and $AntiOxCIN_6$ was evaluated in human hepatocellular carcinoma HepG2 cells. Human hepatocellular carcinoma HepG2 cells were cultured in high-glucose medium composed by Dulbecco's modified Eagle's medium (DMEM; D5648) supplemented with sodium pyruvate (0.11 g/L), sodium bicarbonate (1.8 g/L) and 10% fetal bovine serum (FBS) and 1% of antibiotic penicillin-streptomycin 100× solution. Cells were maintained at 37° C. in a humidified incubator with 5% $CO_2$. HepG2 cells were seeded at density of $4\times10^4$ cells/mL and grown for 24 hours before treatment.

In an embodiment the cytotoxicity screening was performed as follows: cells were placed on 48-well plate ($2\times10^4$ cells/500 μL) and then were incubated during 48 hour with $AntiOxCIN_4$ and $AntiOxCIN_6$ concentrations ranging 25 μM to 500 μM or 0.5 μM to 25 μM, respectively. After incubation, sulforhodamine B (SRB) assay was used for cell density determination based on the measurement of cellular protein content. Briefly, after incubation, the medium was removed and wells rinsed with PBS (1×). Cells were fixed by adding 1% acetic acid in 100% methanol for at least 2 hours at −20° C. Later, the fixation solution was discarded and the plates were dried in an oven at 37° C. Two hundred and fifty microliters of 0.5% SRB in 1% acetic acid solution was added and incubated at 37° C. for 1 h. The wells were then washed with 1% acetic acid in water and dried. Then, 500 μl of Tris (pH 10) was added and the plates were stirred for 15 min. Finally, 200 μl of each supernatant was transferred in 96-well plates and optical density was measured at 540 nm. Data are means±SEM of four independent experiments and the results are expressed as percentage of control (control=100%), which represents the cell density without any treatment in the respective time point.

In an embodiment, the cellular antioxidant profile of $AntiOxCIN_4$ and $AntiOxCIN_6$ was evaluated in human hepatocellular carcinoma HepG2 cells.

In an embodiment, the cellular antioxidant screening was performed as follows: cells were placed on 48-well plate ($2\times10^4$ cells/500 μL) and pre-incubated with non-toxic concentrations of $AntiOxCIN_4$ (100 μM) or $AntiOxCIN_6$ (2.5 μM) for 1 hour. After the incubation time, cells were exposed to oxidative stress conditions by the addition of 250 μM $FeSO_4$ or 250 μM $H_2O_2$ for 48 hours. At the end of incubation time, SRB assay was used for cell density determination as previously described. Data are means±SEM of four independent experiments. The results are expressed as percentage of control (control=100%), which represents the cell density without any treatment in the respective time point. The oxidant stressors resulted into a significant inhibition of cell proliferation, 30% and 42%, respectively, when compared with control.

In an embodiment, the cellular morphological alterations induced by AntiOxCIN$_4$ and AntiOxCIN$_6$ in human hepatocellular carcinoma HepG2 cells were assessed using vital epifluorescence microscopy.

In an embodiment, the detection of morphological alterations, including chromatin condensation and mitochondrial polarization and distribution by vital epifluorescence microscopy was performed as follows: cells were placed in 6-well plates with a glass coverslip per well ($8 \times 10^4$ cells/2 mL) and then treated with non-toxic concentrations of AntiOxCIN$_4$ or AntiOxCIN$_6$ for 48 hours. Thirty minutes prior the end of the incubation time, the mitochondrial network was stained with TMRM (100 nM) while nuclei were stained with Hoechst 33342 (1 µg/mL), to detect apoptotic chromatin condensation, in HBSS (NaCl 137 mM, KCl 5.4 mM, NaHCO$_3$ 4.2 mM, Na$_2$HPO$_4$ 0.3 mM, KH$_2$PO$_4$ 0.4 mM, CaCl$_2$ 1.3 mM, MgCl$_2$ 0.5 mM, MgSO$_4$ 0.6 mM, and D-glucose 5.6 mM, pH 7.4) at 37° C. under dark conditions. Glass coverslips were removed from the wells and placed on glass slides with a drop of mounting medium. The cell images were acquired using a Zeiss LSM 510Meta microscope and analysed with ImageJ software 1.49v. The probes were maintained with cells during the imaging procedure and four image fields were randomly collected from each well. The images are representative of three independent experiments.

In an embodiment, all the biological data was analyzed as follows: in GraphPad Prism 5.0 software (GraphPad Software, Inc.), with all results being expressed as means±SEM for the number of experiments indicated. Data were analyzed by the student's t-test for comparison of two means, and one-way ANOVA with Dunnet multiple comparison post-test. The last test was used to compare more than two groups with one independent variable. Significance was accepted with *$P<0.05$, $P<0.01$, *$P<0.0005$, ****$P<0.0001$.

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the disclosure encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects are excluded are not set forth explicitly herein.

The above described embodiments are combinable.

The following claims further set out particular embodiments of the disclosure.

All references recited in this document are incorporated herein in their entirety by reference, as if each and every reference had been incorporated by reference individually.

REFERENCES

1. Murphy M P. Antioxidants as therapies: can we improve on nature? *Free Radical Biology and Medicine* 2014, 66: 20-23.
2. Benfeito S, Oliveira C, Soares P, Fernandes C, Silva T, Teixeira J, et al. Antioxidant therapy: still in search of the 'magic bullet'. *Mitochondrion* 2013, 13(5): 427-435
3. Wallace D C, Fan W, Procaccio V. Mitochondrial energetics and therapeutics. *Annual review of pathology* 2010, 5: 297-348.
4. Smith R A, Hartley R C, Cocheme H M, Murphy M P. Mitochondrial pharmacology. *Trends in pharmacological sciences* 2012, 33(6): 341-352.
5. Teixeira J, Soares P, Benfeito S, Gaspar A, Garrido J, Murphy M P, et al. Rational discovery and development of a mitochondria-targeted antioxidant based on cinnamic acid scaffold. *Free radical research* 2012, 46(5): 600-611.

The invention claimed is:
1. A compound of formula I

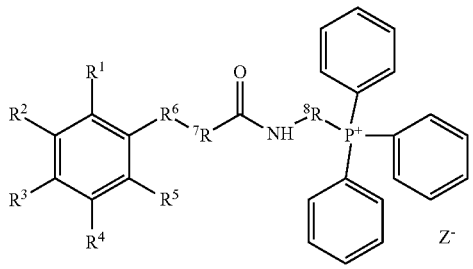

or a pharmaceutically acceptable salt, solvate, hydrate, tautomer, or stereoisomer thereof, wherein $R^1$, $R^2$, $R^3$, $R^4$, $R^5$, $R^6$, $R^7$ and $R^8$ are independently selected from each other;

$R^1$, $R^2$, $R^3$, $R^4$ and $R^5$ are selected from H, halogen, hydroxyl, methyl, methoxyl, amino, carboxylic acid, or nitro group;

$R^6$, $R^7$ are an alkyl chain, an alkenyl chain, an alkynyl chain, a substituted aryl or a cyclic ring;

wherein $R^8$ is a $C_6$-$C_{18}$ alkyl chain, a $C_6$-$C_{18}$ alkenyl chain, or a $C_6$-$C_{18}$ alkynyl chain;

a bond between $R^6$ and $R^7$ is a single bond, a double bond or a triple bond and with the proviso that wherein the bond between $R^6$ and $R^7$ is a double bond, $R^3$=$R^2$ are different from OH, and $R^1$=$R^4$ are different from H, and $R^6$=$R^7$ are different from methyl, and $Z^-$ is an anion.

2. The compound of claim 1 wherein the bond between $R^6$ and $R^7$ is a single bond or a double bond.

3. The compound of claim 1 wherein the alkyl chain, the alkenyl chain or the alkynyl chain is a $C_2$-$C_{30}$ chain.

4. The compound of claim 1 wherein the alkyl chain, the alkenyl chain or the alkynyl chain is a $C_2$-$C_{14}$ chain.

5. The compound according to claim 4 wherein the alkyl chain is a $C_6$ alkyl chain, a $C_7$ alkyl chain, a $C_8$ alkyl chain, a $C_9$ alkyl chain, or a $C_{10}$ alkyl chain.

6. The compound according to claim 1 wherein the substituted aryl is an alkane-aryl substituted, alkene-aryl substituted, or alkyne-aryl substituted.

7. The compound according to the claim 6 wherein the alkane-aryl substituted, alkene-aryl substituted, or alkyne-aryl substitution is $C_1$-$C_6$-alkyl, $C_3$-$C_8$-cycloalkyl, $C_6$-$C_{10}$-aryl, $C_1$-$C_6$-alkoxy, $C_6$-$C_{10}$-aryloxy, $C_6$-$C_{10}$-aryl-$C_1$-$C_8$-alkoxy, hydroxyl, $CO_2H$, $C_1$-$C_6$-alkoxycarbonyl, $C_6$-$C_{10}$-aryloxycarbonyl, $C_6$-$C_{10}$-aryl-$C_1$-$C_8$-alkoxycarbonyl, $C_1$-$C_6$-alkylcarbonyl, $C_6$-$C_{10}$-arylcarbonyl, $C_6$-$C_{10}$-aryl-$C_1$-$C_8$-alkylcarbonyl, $C_1$-$C_6$-alkylcarboxy, $C_6$-$C_{10}$-arylcarboxy, $C_1$-$C_6$-alkylmercaptyl, $C_6$-$C_{10}$-arylmercaptyl, $C_1$-$C_6$-alkylmercaptocarbonyl, $C_3$-$C_8$-cycloalkylmercaptocarbonyl, $C_6$-$C_{10}$-arylmercaptocarbonyl, $C_1$-$C_6$-alkylmercaptocarboxy, $C_6$-$C_{10}$-arylmercaptocarboxy, $C_1$-$C_6$-alkylsulfonyl, $C_6$-$C_{10}$-arylsulfonyl, $C_1$-$C_6$-alkylsulfoxy, or $C_6$-$C_{10}$-arylsulfoxy;

each of which is optionally substituted once or several times by $C_1$-$C_6$-alkyl, $C_1$-$C_6$-alkoxy, COOH; $CONH_2$, substituted once or twice with $C_1$-$C_6$-alkyl; $SO_3H$, amino, thiol, hydroxyl, nitro, cyano, fluoro, chloro, bromo, iodo, $CF_3$ or $OCF_3$;

wherein several of these optional substituents are combined to form anellated saturated, unsaturated or aromatic homo- or hetero-ring systems; or a saturated, unsaturated or aromatic heterocycle substituted once or several times by $C_1$-$C_6$-alkyl, $C_1$-$C_6$-alkoxy, COOH; $CONH_2$, substituted once or twice.

8. The compound according to claim 1 wherein the cyclic ring is a cyclopropane, cyclobutane, cyclopentane, or cyclohexane.

9. The compound according to claim 1 wherein $Z^-$ is selected from the following list: alkyl sulfonate, aryl sulfonate, nitrate or a halogen, wherein said halogen is F, Cl or Br.

10. The compound according to claim 9 wherein the alkyl sulfonate or aryl sulfonate is selected from the group consisting of: methanesulfonate, p-toluenesulfonate, ethanesulfonate, benzenesulfonate and 2-naphthalenesulfonate.

11. The compound according to claim 1 wherein the halogen is F, Cl or Br.

12. The compound according to claim 1 wherein $R^1$ and $R^5$ are H.

13. The compound according to claim 1 wherein $R^2$ and $R^3$ are OH.

14. The compound according to claim 1 wherein $R^4$ is H or OH.

15. The compound according to claim 1 wherein $R^6$ and $R^7$ are a $C_1$ alkyl chain.

16. A compound of the following name:
(E)-(6-(3-(3,4-dihydroxyphenyl)prop-2-enamido)hexyl) triphenylphosphonium methanesulfonate.

17. A compound of the following chemical name:
(E)-(8-(3-(3,4-dihydroxyphenyl)acrylamido)octyl)triphenylphosphonium methanesulfonate.

18. A compound of the following chemical name:
(E)-(6-(3-(3,4,5-trihydroxyphenyl)prop-2-enamido) hexyl)triphenylphosphonium methanesulfonate.

19. A compound of the following chemical name:
(E)-(8-(3-(3,4,5-trihydroxyphenyl)acrylamido)octyl)triphenylphosphonium methanesulfonate.

20. A compound of the following chemical name:
(E)-(10-(3-(3,4-dihydroxyphenyl)acrylamido)decyl)triphenylphosphonium methanesulfonate.

21. A compound of the following chemical name:
(E)-(10-(3-(3,4,5-trihydroxyphenyl)acrylamido)decyl)triphenylphosphonium methanesulfonate.

22. A pharmaceutical composition comprising the compound according to claim 1 and a pharmaceutically acceptable carrier, adjuvant, excipient, diluent or mixtures thereof.

* * * * *